US006652724B2

(12) United States Patent
Michael et al.

(10) Patent No.: US 6,652,724 B2
(45) Date of Patent: Nov. 25, 2003

(54) AUTOMATED APPARATUS FOR SEPARATING A BIOLOGICAL SAMPLE FROM A TWO DIMENSIONAL ELECTROPHORESIS GEL

(75) Inventors: Samuel Michael, Silver Spring, MD (US); Jack Goodman, Lusby, MD (US); N. Leigh Anderson, Washington, DC (US)

(73) Assignee: Large Scale Proteomics Corporation, Germantown, MD (US)

( * ) Notice: Subject to any disclaimer, the term of this patent is extended or adjusted under 35 U.S.C. 154(b) by 22 days.

(21) Appl. No.: 09/859,664

(22) Filed: May 18, 2001

(65) Prior Publication Data

US 2002/0146832 A1 Oct. 10, 2002

Related U.S. Application Data

(60) Provisional application No. 60/287,797, filed on Apr. 30, 2001, and provisional application No. 60/281,000, filed on Apr. 4, 2001.

(51) Int. Cl.[7] .................... C25B 11/00; C25B 13/00; C25B 9/00
(52) U.S. Cl. ............ 204/613; 204/462; 204/466; 204/616; 204/467; 204/618; 422/99
(58) Field of Search ............... 204/462, 613, 204/466, 616, 467, 618, 414, 464, 463; 73/863, 863.33, 863.32; 435/287.1, 287.3; 422/63, 99–104; 436/43; 901/18, 15, 17

(56) References Cited

U.S. PATENT DOCUMENTS

| 4,035,377 | A | * | 7/1977 | Detroy ................ 204/619 |
| 4,897,015 | A | * | 1/1990 | Abbe et al. ........... 414/744.8 |
| 5,458,749 | A | | 10/1995 | Stone et al. |
| 5,516,402 | A | | 5/1996 | Sarrine et al. |
| 5,587,062 | A | | 12/1996 | Togawa et al. |
| 5,592,289 | A | * | 1/1997 | Norris ................. 356/244 |
| 5,626,735 | A | * | 5/1997 | Chu .................... 204/606 |
| 5,645,800 | A | | 7/1997 | Masterson et al. |
| 5,865,975 | A | | 2/1999 | Bishop |
| 5,949,899 | A | | 9/1999 | Ng |
| 5,985,214 | A | | 11/1999 | Stylli et al. |
| 5,993,627 | A | | 11/1999 | Anderson et al. |
| 6,060,022 | A | | 5/2000 | Pang et al. |
| 6,064,754 | A | | 5/2000 | Parekh et al. |
| 6,179,980 | B1 | * | 1/2001 | Aksberg ............... 204/456 |
| 6,207,031 | B1 | | 3/2001 | Adourian et al. |
| 6,267,927 | B1 | | 7/2001 | Pomar Longedo et al. |
| 6,331,437 | B1 | | 12/2001 | Cohen et al. |
| 2001/0048899 | A1 | * | 12/2001 | Marouiss et al. ....... 422/100 |
| 2002/0018733 | A1 | | 2/2002 | Kapplein et al. |

FOREIGN PATENT DOCUMENTS

| WO | WO 98/23950 | * | 6/1998 |
| WO | WO 99/15875 | | 4/1999 |
| WO | WO 00/493397 | * | 8/2000 |
| WO | WO 00/57153 | | 9/2000 |

* cited by examiner

*Primary Examiner*—Jill Warden
*Assistant Examiner*—Elizabeth Quan
(74) *Attorney, Agent, or Firm*—John C. Robbins; Garrett V. Davis

(57) ABSTRACT

An automated high-throughput system for excising spots or samples from an electrophoresis slab gel includes a computer controlled robotic arm assembly and a sample plate handling assembly for supplying a sample plate to a loading station. The computer is connected to a scanner and imaging device to identify selected sample locations on the slab gel and to direct the robotic arm to the selected locations for excising the gel spots. The cutting assembly includes a removable tray for supporting the slab gel during the cutting process and is coupled to the automated sample plate handling assembly. The sample plate handling assembly delivers a multiwell plate to the cutting assembly for receiving the gel spots. The removable tray cooperates with a scanner for identifying protein spots and includes a positioning device to position the tray in the scanner and the cutting assembly in selected locations to coordinate the scanned image with the cutting process.

44 Claims, 17 Drawing Sheets

AUTOMATED APPARATUS FOR SEPARATING A BIOLOGICAL SAMPLE FROM A TWO DIMENSIONAL ELECTROPHORESIS GEL

This Application claims benefit of Prov. No. 60/281,000 filed Apr. 4, 2001 and claims benefit of Prov. No. 60/287,797 filed Apr. 30, 2001.

FIELD OF THE INVENTION

The present invention is directed to a method and apparatus for automatically identifying the location of a biological sample in an electrophoresis gel and transferring the sample to a sample plate. More particularly, the invention is directed to a computer assisted method and to a computer controlled apparatus for excising a gel spot from an electrophoresis gel slab and transferring the gel spot to a multiwell sample plate.

BACKGROUND OF THE INVENTION

Genomes provide the sequence information required to construct proteins that are the working parts of living cells. Genomes and genes are linear constructs composed of four different nucleotides arranged in triplet condons that specify the order and identity of the approximately 20 different amino acids that make up proteins. The nucleic acids are chemically very similar, and are arranged in very long contiguous sequences with intervening non-coding regions. For analysis, nucleic acids must be cut up into fragments of tractable length using shearing forces or restriction enzymes which cut the nucleic acid at specific known sites.

Proteins are made of amino acid subunits that have a range of different isoelectric points, molecular weights, and solubility or hydrophobicity characteristics. The synthesized peptides have exactly defined lengths, and roll up or are assembled into proteins of well defined molecular weights. The estimated 100,000 different primary proteins in man have a range of charge densities and isoelectric points, solubilities, and surface characteristics not found in nucleic acids. Further, proteins have a range of surface conformations which mediate specific interactions between proteins, between proteins and nucleic acids, and, in the form of enzymatically active sites, between low molecular weight metabolites, and all the various types of macromolecules found in cells and foodstuffs. Proteins are the molecular machines that carry out the panoply of syntheses, disassemblies and degradations, immunochemical defense reactions, and paratactic interactions that underlie the assembly of membranes and subcellular organelles.

There is a need for analytical methods that allow a large fraction of the total number of proteins present in a cell or tissue to be detected and quantitated. The quantitative analysis of large sets of proteins that have such a wide variety of functions, sizes, conformation, activities, solubilities, and charge characteristics is both a centrally important challenge, and an exceedingly difficult problem. The problem is rendered even more difficult by the requirement that analysis detecting thousands of proteins per analyses be done in parallel on relatively large numbers of samples in a reasonable time to do experimental toxicological and pharmacological studies.

The electrophoretic mobility of a non-denatured protein is a function of the surface charges of either the monomeric protein or the sum of the surface charges of the subunits, and these are generally used under rate-zonal conditions, i.e., under conditions where the proteins move through a gel or other support at one pH. The distance traveled is a function of the charge to mass ratio, and a function of electrophoresis time. Second dimension separations are done in gradient gels of decreasing pore size such that proteins move until movement essentially ceases as the protein reach pore sizes that prevent further movement. Experimental attempts to develop two dimensional methods based on these parameters using non-denaturing conditions have not yielded the resolution required.

Two-dimensional methods involving denaturing conditions have been explored and widely adopted. The initial separation is done in concentrated urea in the presence of ampholytes which are a heterogeneous mixture of synthetic polymers having wide variation in the ratio of acidic to basic groups. When these are subjected to an electrical field in a gel, the ampholytes sort themselves out into a continuous series based on the isoelectric point. Proteins move along the gel until they reach their own isoelectric point and stop. Further, since the proteins are denatured and unrolled, their isoelectric points reflect the sum of all of the charged groups in the protein, whether previously external or internal in the native state. The isoelectric point determination in such a separation can be calculated from the amino acid composition of the protein, and is a valuable parameter for protein classification.

The second dimensional separation is based on the length (and hence the mass) of the unrolled denatured protein and takes place in the following way. Proteins from the isoelectric separation are exposed to a highly charged detergent which has attached the longest paraffin chain which will remain extended in solution, and not fold back on itself. Sodium dodecyl sulfate (SDS) is the detergent of choice, and in solution will uniformly coat unrolled polypeptide chains, and attach to them by hydrophobic linkages, leaving the highly charged sulfate groups on the surface. The result is particles of approximately rod shape having approximately equal charge-to-mass ratios. Particles having equal charge-to-mass ratios move at the same rate in electrical fields, so that all proteins covered with SDS should have equal mobility in solution. However, if electrophoresis of such particles is done in a microporous gel, then larger particles will be retarded relative to smaller ones.

In practice, the resolutions of these two separate methods are quite high. At least 150 proteins can be resolved from a suitable mixture by isoelectric focusing, and an equal number resolved from a suitable protein mixture by SDS electrophoresis. If the two processes can be mated together in a two-dimensional array, the final resolution should be the product of the resolution of the two methods separately, i.e., $150^2$ or 22,500. Experimentally, as many as 5,000 proteins have been resolved in large two-dimensional electrophoresis gels, and the theoretical resolution of current electrophoresis as calculated from spot sizes, and the number of spots which could theoretically be packed into the gel area used is around 30,000.

It is quite evident that a key step in the high-resolution two-dimensional electrophoresis technique using isoelectric focusing followed by SDS electrophoresis in the second dimension is mating the two methods together without the loss of resolution inherent in collecting and separately analyzing fractions.

Experimentally, isoelectric focusing is done under temperature controlled conditions in glass tubes (ISO tubes) having an internal diameter of approximately 0.5–2 mm, and approximately 30 cm long. ISO tubes are then attached to a small syringe full of water or buffer solution, and the gels extruded by hand along the top of a second-dimension gel cast between two glass plates. An empty space is typically formed between the top of the gel and the top of the plates. The gels are carefully extruded into this space by a double movement in which the syringe plunger is moved to extrude the gel as the ISO tube containing the gel is moved laterally along the top of the second dimension gel.

The molecules of the test sample migrate through the second dimension gel under the influence of an electric current to isolate the biomolecules. The gel is stained with various stains, such as silver or fluorescent compounds, to visualize the biomolecules. The stained biomolecules are then cut from gel and analyzed by various processes. Typically, the biomolecules are manually cut from the gel slab in the form of a gel spot. The gel spot is then placed in a suitable container. Typically, a single biological sample can be isolated into hundreds of biomolecules that must be manually cut from the gel slab. Accordingly, there is a continuing need in the industry for an improved method and apparatus for cutting samples from a gel slab.

SUMMARY OF THE INVENTION

The present invention is directed to an automated apparatus for separating a sample or gel spot from a second dimension electrophoresis gel and transferring the gel spot to a storage container. More particularly, the invention is directed to a computer assisted method and to a computer controlled apparatus for identifying a gel sample containing selected biomolecules in a second dimension electrophoresis gel and transferring the gel sample to a suitable vessel, such as a multiwell sample plate.

Accordingly, a primary aspect of the invention is to provide a method and apparatus for identifying and excising a sample from an electrophoresis gel and transferring the sample to a sample plate.

Another aspect of the invention is to provide a computer controlled robotic arm operatively connected to a computer, where the computer receives an image signal to identify the location of selected samples in an electrophoresis gel and directs the robotic arm to cut the selected samples from the electrophoresis gel.

A further aspect of the invention is to provide an assembly for identifying and separating a sample from an electrophoresis gel, where the assembly includes a remote scanning device and an excising device to excise selected samples from the gel that are identified by the scanning device.

Still another aspect of the invention is to provide a method and apparatus for separating a biological sample from a gel where the gel is supported by a tray that is removably coupled to a gel cutting assembly.

A further aspect of the invention is to provide a method and apparatus for identifying and separating a sample from an electrophoresis gel where the gel is supported on a tray and where the tray can be received in an imaging device to capture an image of the gel and identify selected samples on the gel.

Another aspect of the invention is to provide a tray for supporting an electrophoresis gel where the tray is receivable in an imaging device and receivable in a computer controlled sample cutting device.

Still another aspect of the invention is to provide a tray for supporting an electrophoresis gel where the tray includes a positioning member for positioning the tray in a predetermined location in an imaging device and for positioning the tray in a cutting device for identifying and cutting selected samples from the gel.

A further aspect of the invention is to provide a tray for supporting an electrophoresis gel slab and a carrier device for transporting the gel, where the gel is supported on the tray in a manner to scan an image of the gel and to cut a selected gel sample from the gel slab.

Another aspect of the invention is to provide a tray for supporting an electrophoresis gel where the tray includes at least one aperture for coupling to a computer controlled robotic arm for transporting the tray between work stations.

A further aspect of the invention is to provide a tray for supporting an electrophoresis gel during an imaging process and during a sample cutting process, where the tray includes a first recess for receiving a robotic arm assembly for transporting the tray between work stations and a second recess for cooperating with a robotic arm assembly for loading and unloading a gel onto the tray.

Still another aspect of the invention is to provide a computer controlled assembly for excising a sample from an electrophoresis gel and transferring the sample to a respective well of a multiwell plate where the multiwell plate is delivered from a supply magazine.

Another aspect of the invention is to provide a computer controlled assembly having a conveying apparatus for supplying a sample container from a magazine to an electrophoresis gel cutting device and for conveying the sample container to a storage magazine after receiving a predetermined number of samples.

The various aspects of the invention basically provide an automated apparatus for identifying a sample containing a macromolecule in an electrophoresis gel, excising the sample, and transferring the sample to a multiwell plate. The apparatus includes a computer to control a robotic arm that is able to remove a gel sample or gel spot at a selected location on an electrophoresis gel containing the separated macromolecules. The computer is operatively connected to a plate handling assembly to deliver a multiwell plate from a supply magazine to the cutting apparatus where the samples that are cut from the gel are deposited in a selected well. The sample plate is then transferred to a storage magazine and an empty sample plate is delivered to the cutting apparatus. The computer is connected to an image or scanning device to identify the location of the macromolecules on the gel and to direct the cutting apparatus to a selected location on the gel.

These and other aspects of the invention are basically attained by providing an apparatus for excising a plurality of samples from an electrophoresis gel. The apparatus comprises a base having a work surface with a loading station dimensioned to support a sample plate having a plurality of sample-receiving wells. A gel support member is removably coupled to the base. The support member has a substantially planar surface for supporting the gel. A computer controlled robotic arm has an operating head for excising a plurality of predetermined samples from the gel while being supported on the gel support member and for transferring the predetermined samples to a respective well of the sample plate. A microprocessor is operatively coupled to the robotic arm for controlling movement of the robotic arm. The microprocessor is programmed to receive a signal for identifying the predetermined samples on the gel, actuating the robotic arm to excise the predetermined samples, and transferring the samples to the respective well of the sample plate.

The aspects of the invention are further attained by providing an apparatus for excising a plurality of biological samples from an electrophoresis gel. The apparatus comprises a base having a work surface with a loading station dimensioned to support an electrophoresis gel and a sample plate having a plurality of sample-receiving wells. An automated sample plate handling assembly is coupled to the base. The plate handling assembly includes a supply magazine for containing a plurality of sample plates, a receiving magazine, and a conveyor for sequentially conveying a sample plate from the supply magazine to the loading station and for conveying the sample plate from the loading station to the receiving magazine. A robotic arm has an operating head for excising a plurality of predetermined samples from the gel and for transferring the excised samples to a respective well of a sample plate positioned in the loading station. A microprocessor is operatively connected to the robotic arm for controlling movement of the robotic arm. The microprocessor is programmed to receive a signal for identifying the predetermined samples on the gel and actuating the robotic arm to excise the respective predetermined samples and transferring the predetermined samples to the respective well of the sample plate.

The aspects of the invention are also attained by providing a computer assisted method for transferring a biological sample from an electrophoresis gel in a cutting assembly to a respective well of a sample plate. A sample plate is delivered from a supply magazine to a sample loading station, where the sample plate includes a plurality of spaced-apart sample wells. A positioning signal is produced indicating the presence of a sample plate in the loading station and transmitting the positioning signal to a computer. An excising signal is produced in the computer and directs a robotic assembly of the cutting assembly in response to the excising signal to excise a biological sample from the electrophoresis gel and transfer the sample to a predetermined well of the sample plate.

The aspects of the invention are still further attained by providing a method of excising and transferring a biological sample from an electrophoresis gel to a respective well of a sample plate. The method comprises the steps of: providing a gel excising apparatus having a top surface for supporting an electrophoresis gel, a loading station dimensioned for supporting a sample plate, a robotic arm having an operating head and being operatively connected to a microprocessor, a supply magazine having a plurality of multiwell sample plates; supplying a sample plate from the supply magazine to the loading station; positioning an electrophoresis gel on the top surface; actuating the robotic arm to excise a predetermined sample from the gel and transferring the excised sample from the gel to a respective well of the sample plate.

The various aspects, advantages and other salient features of the invention will become apparent to one skilled in the art in view of the following detailed description of the invention and the annexed drawings which form a part of this original disclosure.

BRIEF DESCRIPTION OF THE DRAWINGS

The following is a brief description of the drawings, in which.

DETAILED DESCRIPTION OF THE INVENTION

Figure 1:
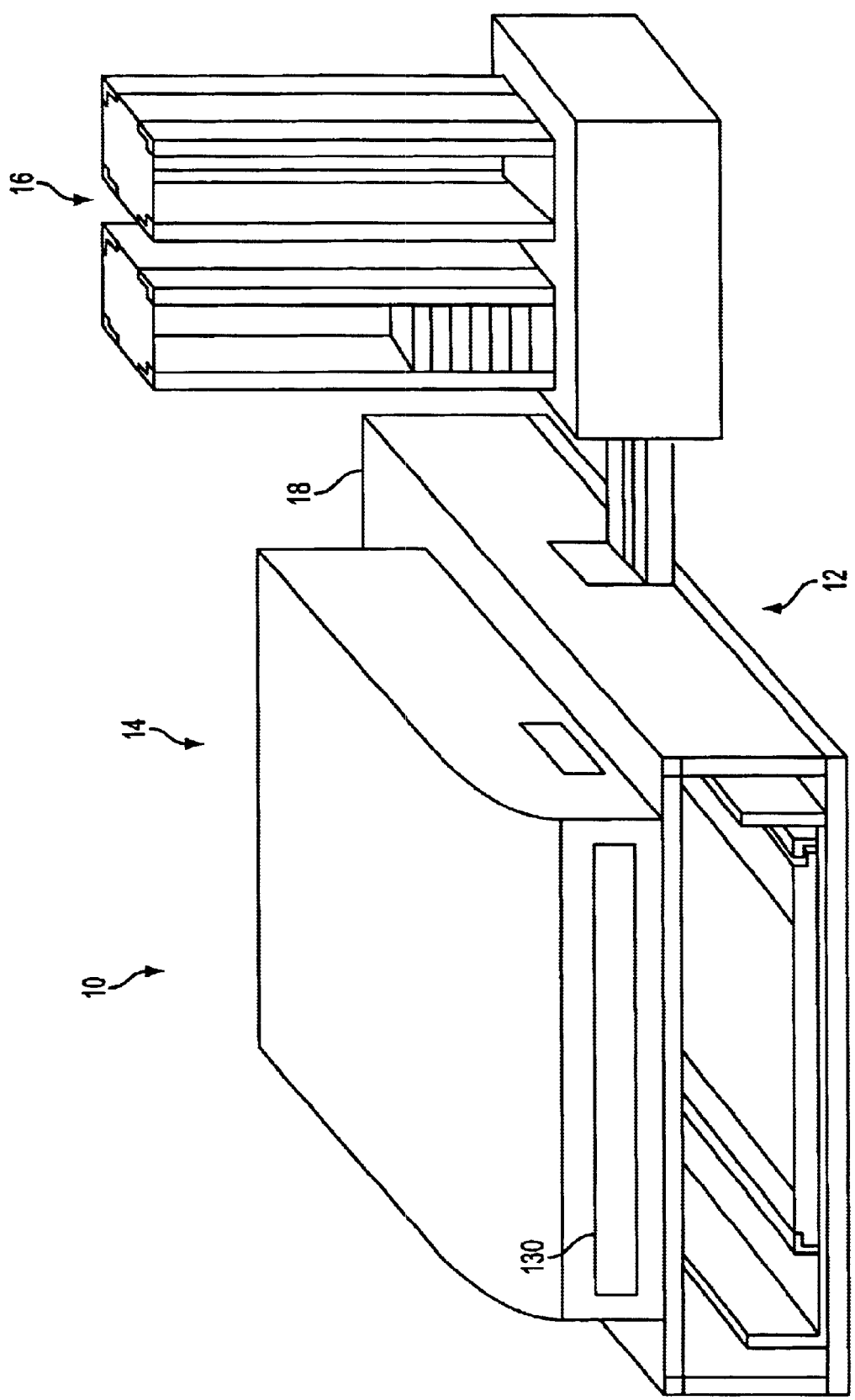
FIG. 1 is a perspective view of the assembly in a first embodiment of the invention showing the imaging device, cutting device, and plate stacking assembly.

The method and apparatus of the invention are used in conjunction with the separation and analysis of macromolecules and particularly proteins. The test sample to be analyzed is subjected to a two dimensional electrophoretic separation that is commonly used in the separation and analysis of proteins. Two dimensional electrophoretic separations typically involve a sequential process of separation steps. A sample, such as a biological sample, is placed at one end of a tube containing a gel, such as a polyacrylamide gel. The ends of the tube are placed in contact with buffer solutions having a selected pH to provide a pH gradient along the length of the gel. An electric current is applied between the ends of the gel, which causes the macromolecules to migrate through the gel until the macromolecules reach their isoelectric point.

The gel from the tube is then subjected to a second dimension separation in a slab gel. The electrophoresis slab gel is molded between two sheets of glass. The gel typically contains a charged detergent such as sodium dodecyl sulfate. The detergents bind to the proteins and unfold the proteins into lengths that are proportional to the length of the peptide chain and proportional to the molecular weight. An electric current is applied to the ends of the slab gel to cause the proteins or other macromolecules to migrate through the gel.

After the two dimensional separation, the slab gel is separated from the glass plates. The gels are typically stained using various stains or dyes. Typical stains include stains that include silver complexes, negative stains where the detergent in the gel is precipitated by zinc ions in regions where the proteins are present, or agents for fluorescently labeling the proteins. The staining or labeling produces a visual pattern that is used to identify the location of the proteins on the gel. A piece of the gel containing the stained proteins is then cut from the slab. An example of a two dimensional gel staining process is disclosed in U.S. Pat. No. 5,993,627 to Anderson et al., which is hereby incorporated by reference in its entirety.

The computer controlled assembly of the present invention coordinates a scanned image of the stained slab gel with a cutting assembly for excising gel spots from the slab gel. The cutting assembly and the imaging or scanning device are controlled to enable the cutting assembly to excise gel spots immediately following a computer analysis of the stained or labeled slab gel. In preferred embodiments, the protein patterns of the slab gel are analyzed by an automated image analysis. The analysis can be a batch process using computer software such as the Kepler®software system. This software subtracts image background, detects and quantifies spots, and matches spot patterns to establish spot identities. A series of records describing the position and abundance for each spot are generated in a computer database for the gel. A computer receives an image signal from the imaging device, processes the signal and generates a cutting signal for directing and controlling the cutting assembly. The movement and operation of the cutting assembly is dictated by the resulting cutting signal to selectively excise gel spots for analysis.

The present invention is primarily directed to a method and apparatus for excising a gel sample containing a macromolecule from an electrophoresis gel slab. More particularly, the invention is directed to a computer controlled assembly for automatically scanning an image of an electrophoresis gel to identify the separated samples and to operate a cutting device for excising the identified samples in the gel.

Figure 2:
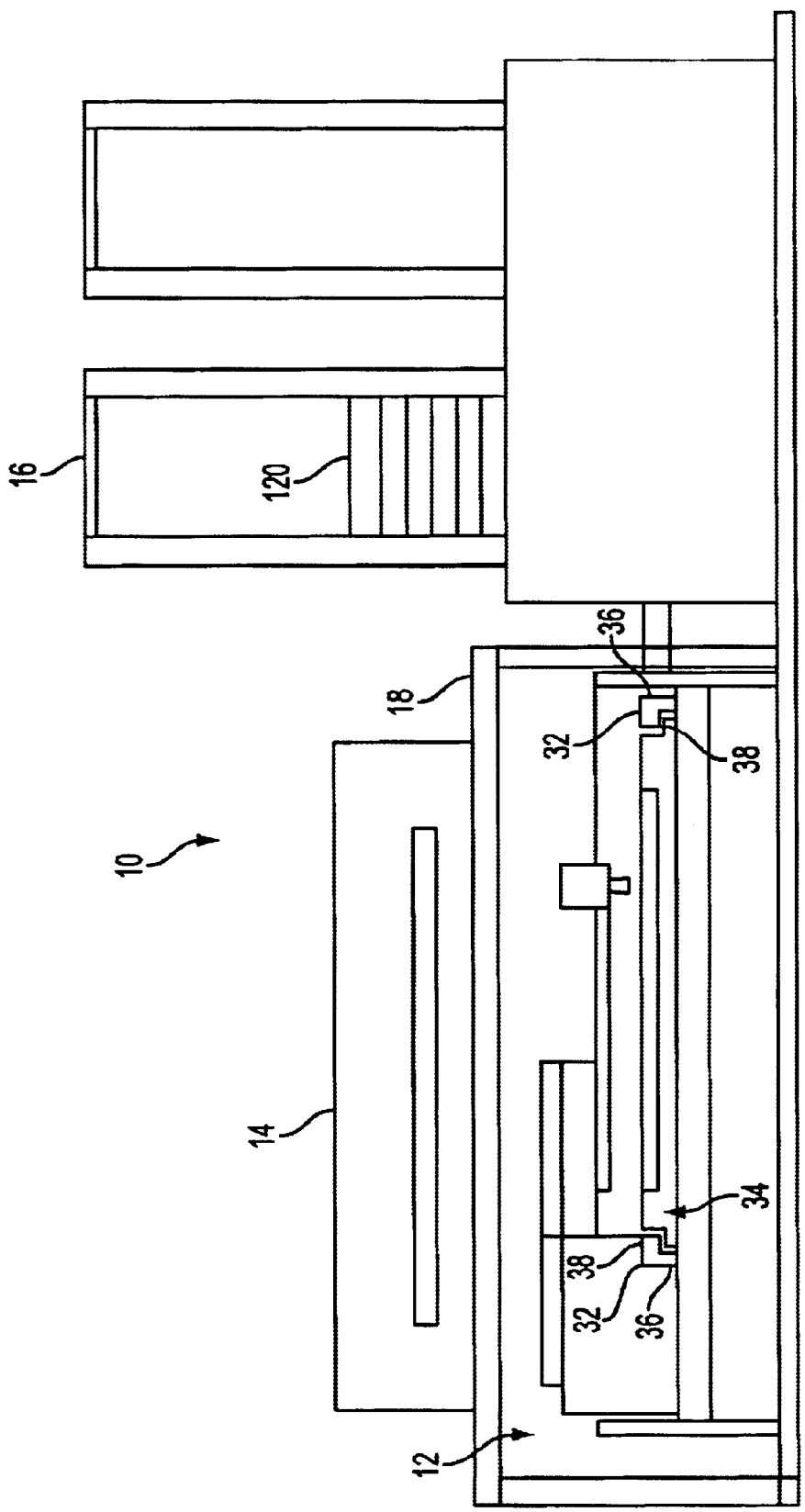
FIG. 2 is a front view of the assembly of FIG. 1.
Figure 3:
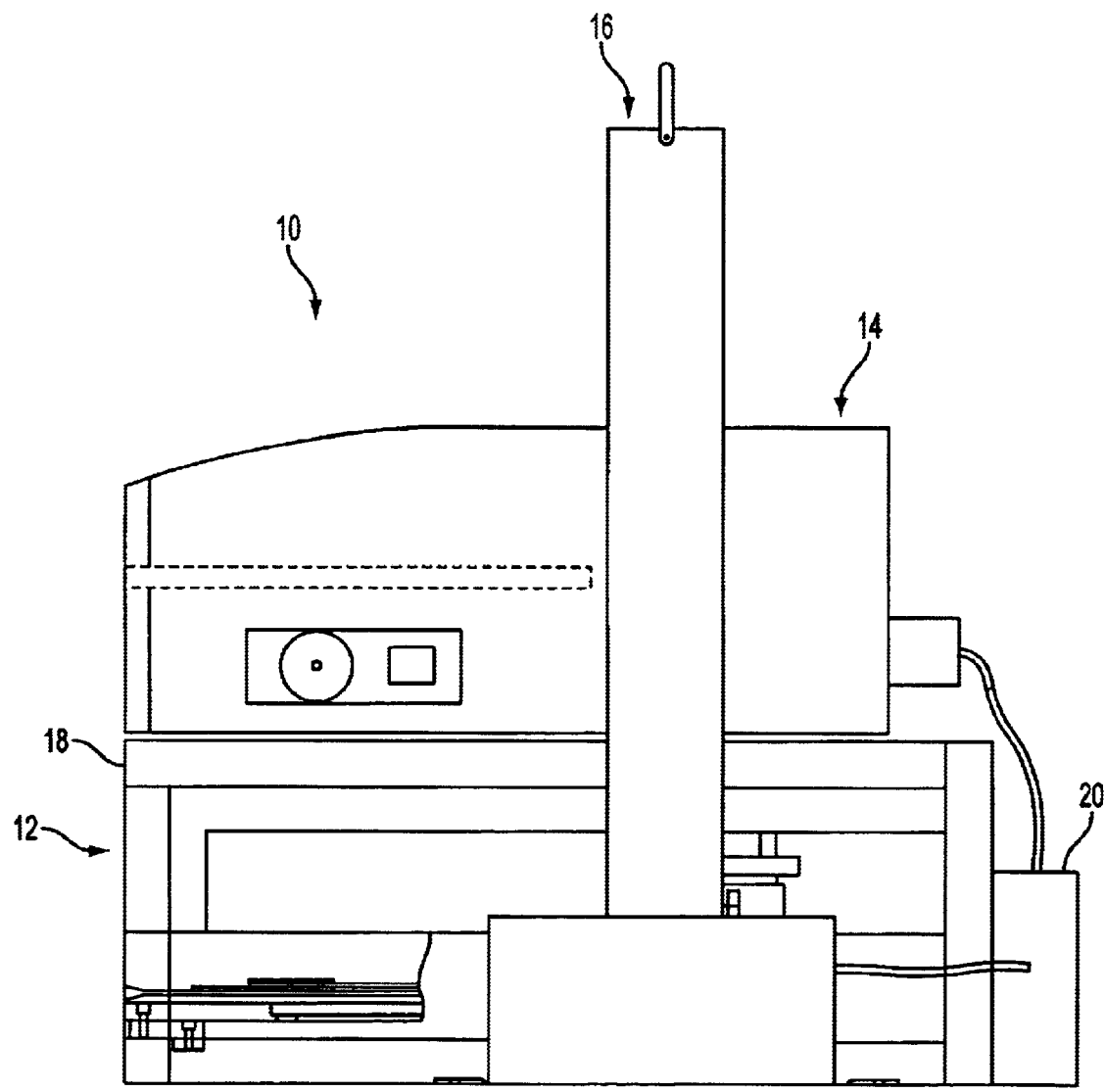
FIG. 3 is a side view of the assembly of FIG. 1.

Referring to FIGS. 1–3, the apparatus 10 of the invention includes a cutting assembly 12, an imaging device 14 and a storage assembly 16. In the embodiment illustrated, cutting assembly 12 and imaging device 14 are placed on a shelf 18 in a stacked relation. In alternative embodiments, cutting assembly 12 and imaging device 14 can be placed in a side by side manner. In one embodiment of the invention, an electrophoresis gel containing macromolecules that have been separated in a two dimensional electrophoresis process is placed in imaging device 14 to obtain an image of the separated macromolecules and to identify the location of the macromolecules on the gel. Imaging device 14 is operatively connected to a computer 20 which stores output data from imaging device 14 corresponding to an image of the electrophoresis gel. The electrophoresis gel is then transferred to cutting assembly 12 where selected samples are excised from the gel and transferred to a suitable storage plate as discussed hereinafter in greater detail.

Figure 4:
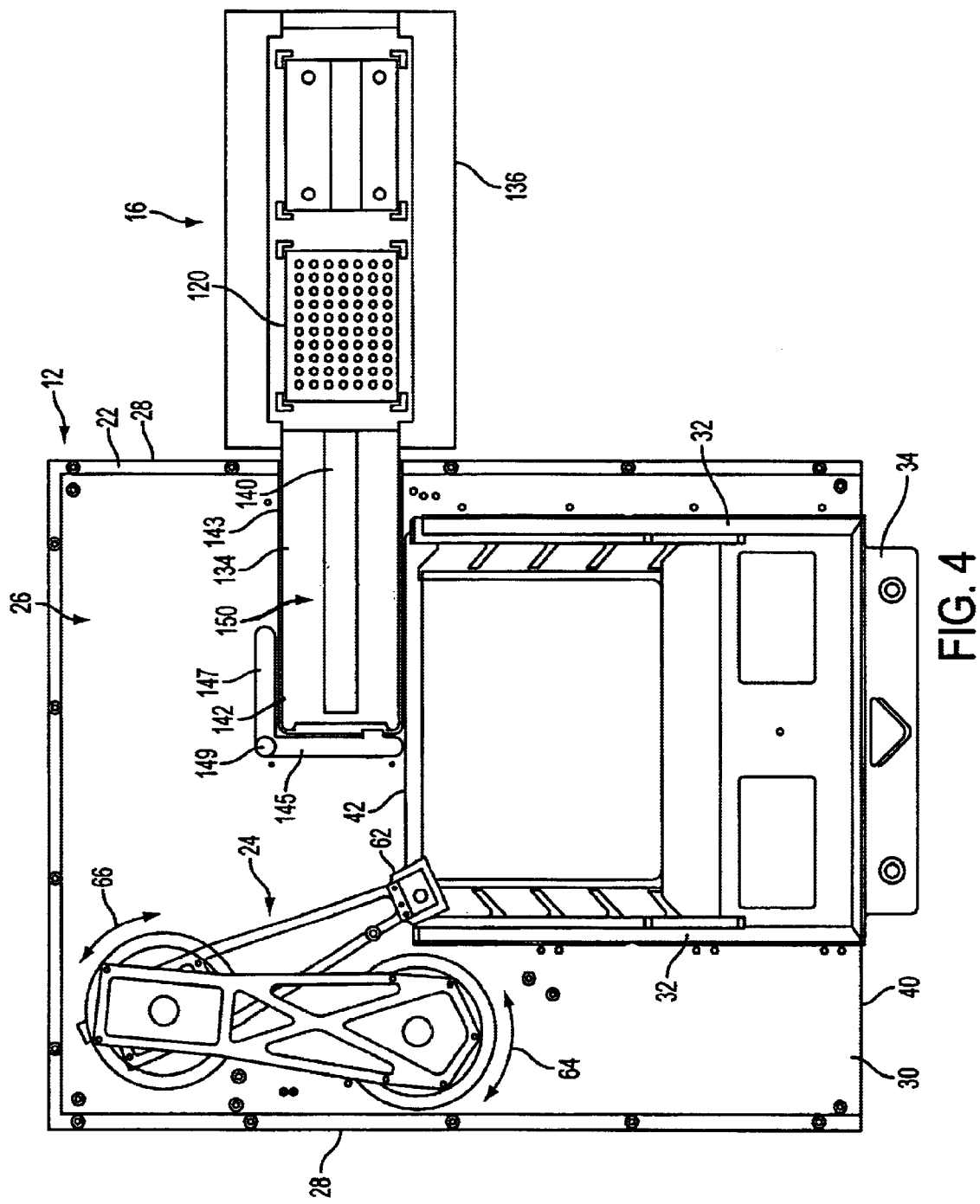
FIG. 4 is a top view of the cutting assembly and stacking assembly in a preferred embodiment of the invention.
Figure 5:
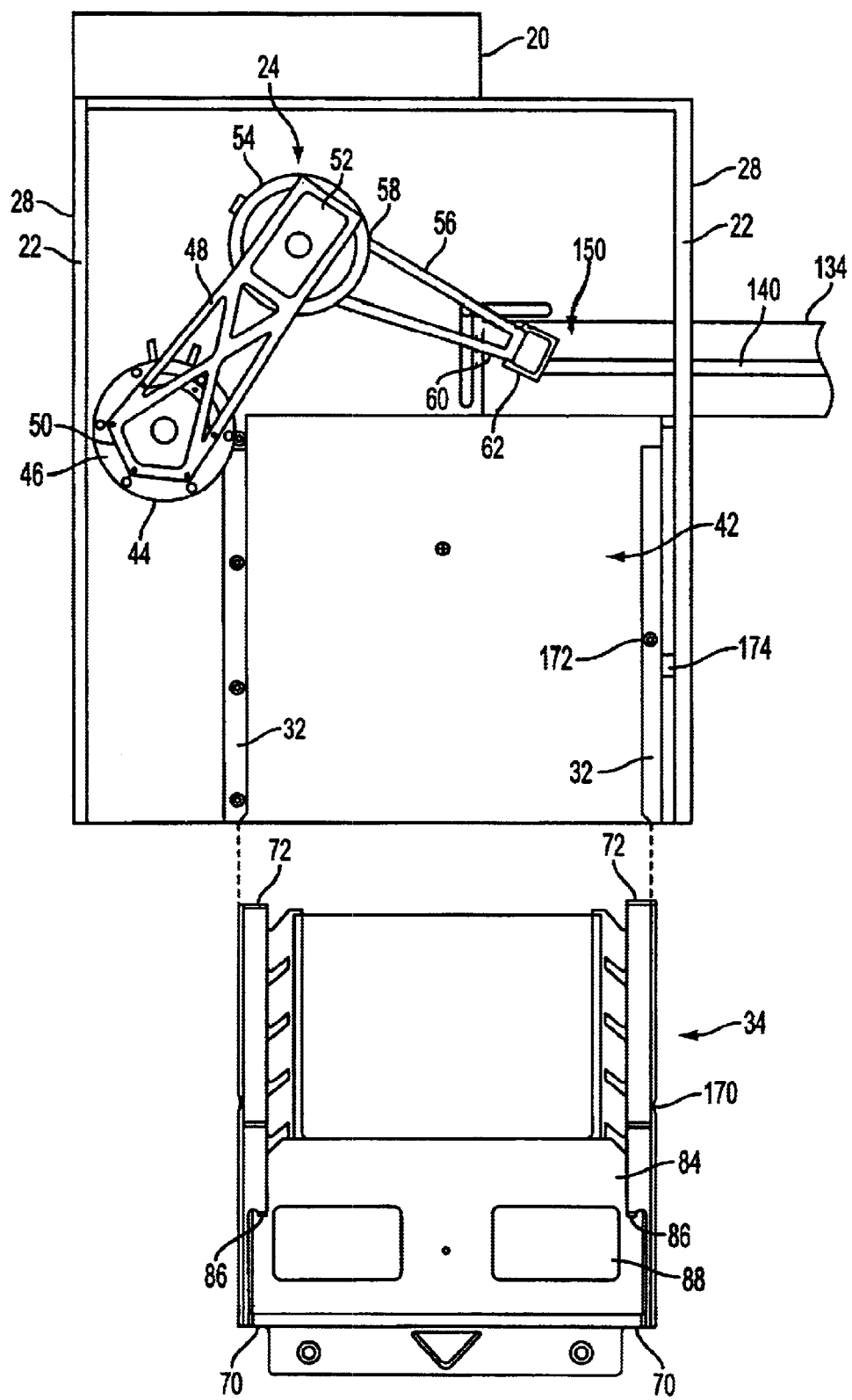
FIG. 5 is an exploded top view of the cutting assembly showing the electrophoresis gel tray and the cutting assembly.

Cutting assembly 12 as shown in FIGS. 4 and 5 includes a housing 22 supporting a robotic arm assembly 24. Housing 22 includes a base 26 defining a work surface with side walls 28 and an open front end 30.

Base 26 includes a pair of spaced-apart guide rails 32 for receiving a gel support member, such as a gel support tray 34. As shown in FIG. 2, guide rails 32 have an upright section 36 and an inwardly extending flange 38 to contain tray 34 and to allow tray 34 to slide into the position shown in FIG. 4. As shown in FIG. 4, guide rails 32 extend from a front edge 40 of base 26 a distance to accommodate tray 34. In one embodiment of the invention, base 26 includes a recessed area 42 between guide rails to receive tray 34. Recessed area 42 has a depth corresponding substantially to the thickness of tray 34 so that a top edge of tray 34 is substantially in the same plane as base 26.

Robotic arm assembly 24 is mounted on base 26 for movement in a direction substantially parallel to base 26. Robotic arm assembly 24 includes a base 44 attached to base 26 of housing 22 adjacent recessed area 42 as shown in FIG. 4. A motor 46 is coupled to base 44 of robotic arm assembly 24. A first movable arm 48 has a first end 50 operatively connected to motor 46 for pivoting first arm 48 about an axis substantially perpendicular to the plane of base 26. First arm 48 has a second end 52 having a second motor 54 coupled thereto. A second arm 56 has a first end 58 operatively coupled to second motor 54 for pivoting about an axis of second motor 54 parallel to the axis of rotation of first motor 46. Second arm 56 includes a second end 60 having a cutting head assembly 62 for excising a sample from an electrophoresis gel.

Robotic arm assembly 24 is operatively connected to computer 20 for directing the movement of first and second arms 48 and 56, respectively, as well as cutting head assembly 62. Computer 20 generates a signal for actuating first motor 46 to pivot first arm 48 about the axis of motor 46 in the direction of arrow 64. Simultaneously, computer 20 produces a signal to actuate second motor 54 to rotate second arm 56 about the axis of motor 54 in the direction of arrow 66. The controlled movement of motors 46 and 54 move cutting head assembly 62 to a selected position with respect to an electrophoresis gel on tray 34 for excising a selected sample from the gel. In a preferred embodiment of the invention, computer 20 receives the imaging signal from imaging device 14, processes the signal to identify the selected locations on the electrophoresis gel, and produces a cutting signal based on polar coordinates for excising the sample from the gel. In alternative embodiments, computer 20 can generate a cutting signal to direct robotic arm assembly 24 based on XY coordinates.

Figure 6:
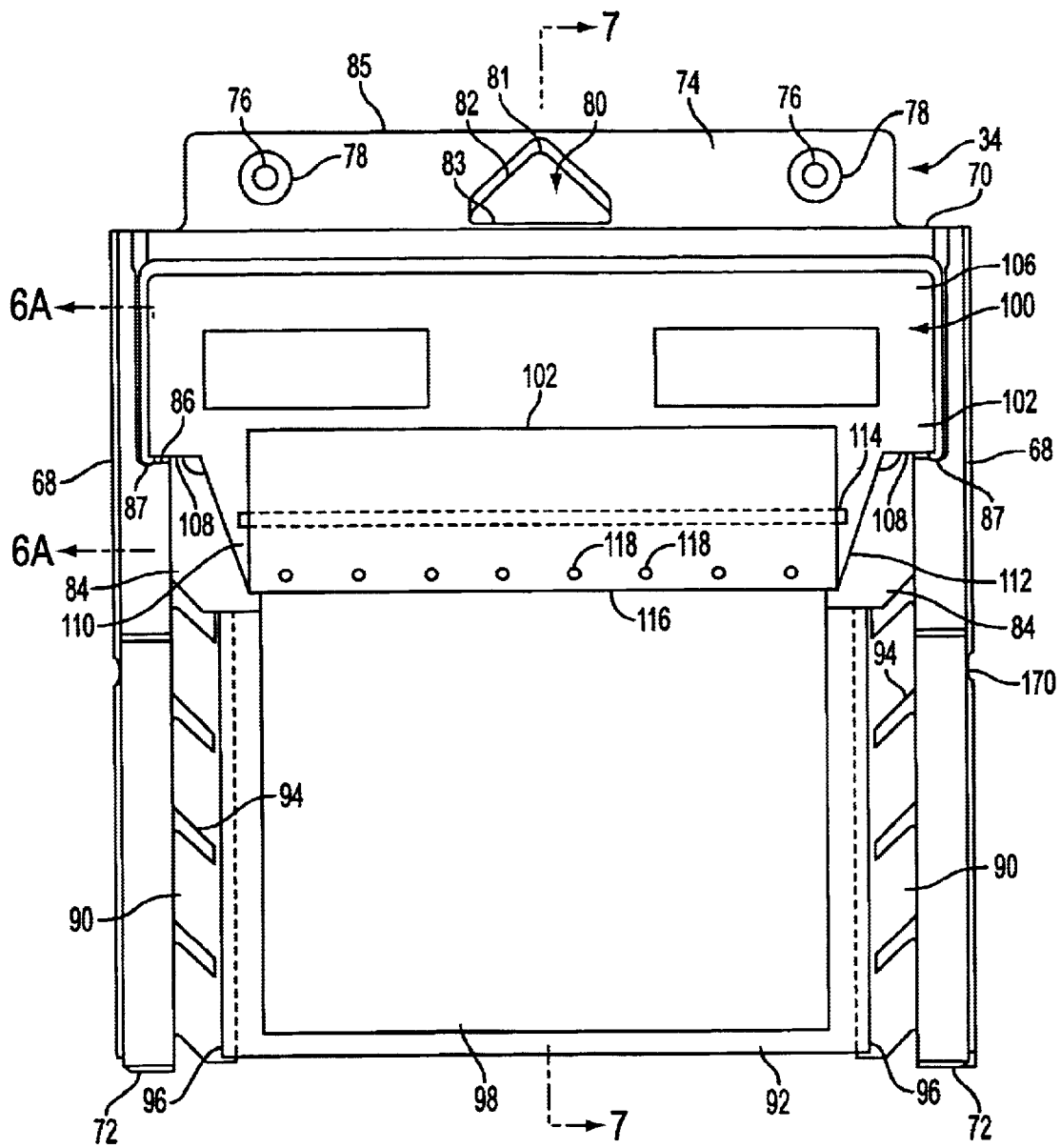
FIG. 6 is a top view of the electrophoresis gel supporting tray showing the gel and gel clamp positioned on the tray.

As shown in FIG. 4, tray 34 is dimensioned to slide between guide rails 32 to position an electrophoresis gel in a preselected position to cooperate with robotic arm assembly 24 for excising the selected samples from the gel. Referring to FIG. 6, tray 34 in one embodiment of the invention has a substantially rectangular shape with parallel side edges 68, a first end 70 and a second end 72. First end 70 of tray 34 includes a handle portion 74 extending outwardly substantially in the plane of tray 34. As shown in FIG. 6, handle 74 has a width slightly less than the overall width of tray 34. Handle 74 in the embodiment illustrated includes two spaced-apart apertures 76 having a circular configuration with a beveled edge 78. Apertures 76 can be provided in handle 74 coupling tray 34 to a suitable storage hanger or robotic device.

A triangular shaped aperture 80 having a beveled edge 82 is formed in handle 74. Preferably, aperture 80 is centrally located in handle 74. Triangular shaped aperture 80 is dimensioned to cooperate with a coupling member of a robotic assembly (not shown) for transferring tray 34 and the associated electrophoresis gel between various work stations. Triangular shaped aperture 80 is oriented with its apex 81 oriented toward an outer edge 85 of handle 74 and with its base 83 spaced inwardly from the outer edge 85.

Tray 34 includes a recessed area 84 at first end 70 extending between side edges 68. As shown in FIG. 5, recessed area 84 has a substantially planar surface with a notched portion 86 adjacent each side edge 68. Two spaced-apart openings 88 are provided in recessed area 84. In the embodiment illustrated, openings 88 have a substantially rectangular configuration.

Figure 6A:
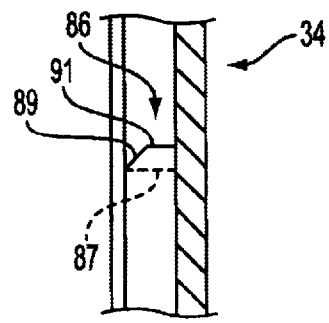
FIG. 6A is a partial cross-sectional view of the tray along line 6A—6A of FIG. 6.

Referring to FIG. 6A, notched portions 86 have a U-shaped recess 87, an inclined top face 89 and a flat portion 91 extending substantially perpendicular to the bottom wall of recessed area 84. Flat portion 91 is dimensioned to support a gel clamp as shown in FIG. 6.

Figure 7:
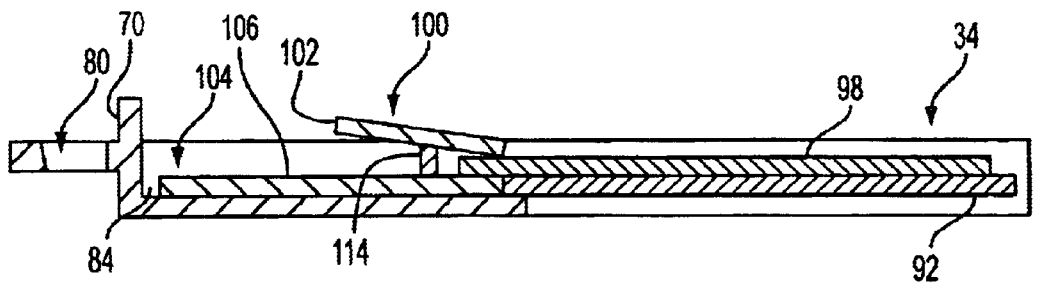
FIG. 7 is a cross-sectional side view of the tray taken along line 7—7 of FIG. 6.

In the embodiment illustrated, side portions 90 extend from recessed area 84 along each side edge 68 to second end 72. Each side portion 90 extends inwardly from the respective side edge 68. A plate member 92 is coupled to side portions 90 on a top surface thereof. As shown in FIG. 7, plate 92 is coupled to the top face of the body of tray 34 to define recessed area 84.

In one embodiment of the invention, side portions 90 of tray 34 are provided with a plurality of spaced-apart ridges 94 that are oriented at an acute angle with respect to the respective side edge 68. As shown in FIG. 6, ridges 94 are oriented at an angle of about 45° and extend from the respective side edge 68 toward second end 72 of tray 34. Ridges 94 terminate a short distance from a side edge 96 of plate 92. Ridges 94 are oriented to direct a washing liquid from side edges 68 of tray 34 toward plate 92 when tray 34 is suspended vertically. Ridges 94 enable a rinse liquid to drain away from side edges 68 when suspended vertically to minimize the amount of the rinse liquid remaining on side edges 68 which can be transferred to guide rails 32 of cutting apparatus 12.

Plate 92 is dimensioned to support an electrophoresis gel obtained from a two dimensional electrophoresis separation process as known in the art. Plate 92 is substantially flat and has a planar top surface for supporting the gel. As shown in FIGS. 5 and 6, plate 92 has side edges 96 that overlie side portions 90 for coupling plate 92 to side portions 90. In a preferred embodiment of the invention, plate 92 is made from a sheet of glass. Tray 34 is typically made of metal having a corrosion resistant and non-reactive finish to prevent contamination of the electrophoresis gel and reagents that may contact tray 34.

In one embodiment of the invention, tray 34 is dimensioned to receive an electrophoresis gel 98 that is coupled to a gel clamp 100. Gel clamp 100 can be any suitable design of a clamp capable of attaching to an electrophoresis gel slab for suspending the gel vertically and moving the gel between various work stations. In a preferred embodiment of the invention, gel clamp 100 includes a first clamping jaw 102 and a second clamping jaw 104 dimensioned to fit within recessed area 84 of tray 34. First jaw 102 has a top portion 106 having a width to fit within recessed area 84 and includes a shoulder 108 to engage notched portion 86 as shown in FIG. 6. First jaw 102 has a lower portion 110 with a substantially straight bottom edge 112 having a length complementing the dimensions of gel 98. A ridge 114 is coupled to first jaw 102 to define a fulcrum for pivoting second jaw 104 with respect to first jaw 102.

Second jaw 104 has a substantially rectangular shape with a bottom edge 116 complementing bottom edge 112 of first jaw 102. As shown in FIG. 6, second jaw 104 has a width less than the width of first gel clamp 102. First jaw 102 and second jaw 104 include a plurality of spaced-apart magnets 118 oriented along the respective bottom edge 112 and 116. Magnets 118 of first jaw 102 and second jaw 104 are oriented to attract the respective bottom edges 112 and 116 toward each other to provide a clamping pressure sufficient to grip gel 98. Typically, first jaw 102 and second jaw 104 include a textured gripping surface to provide sufficient friction to grip gel 98 and prevent gel 98 from slipping from gel clamp 100 under the clamping pressure provided by magnets 118. As shown in FIG. 7, gel clamp 100 fits in recessed area 84 of tray 34 to enable gel 98 to lie on plate 92. In a preferred embodiment, first clamping jaw 102 of gel clamp 100 has a thickness so that the clamping surface lies substantially in the same plane as the top surface of plate 92 to enable gel 98 to lie on plate 92 substantially without buckling or twisting.

Figure 8:
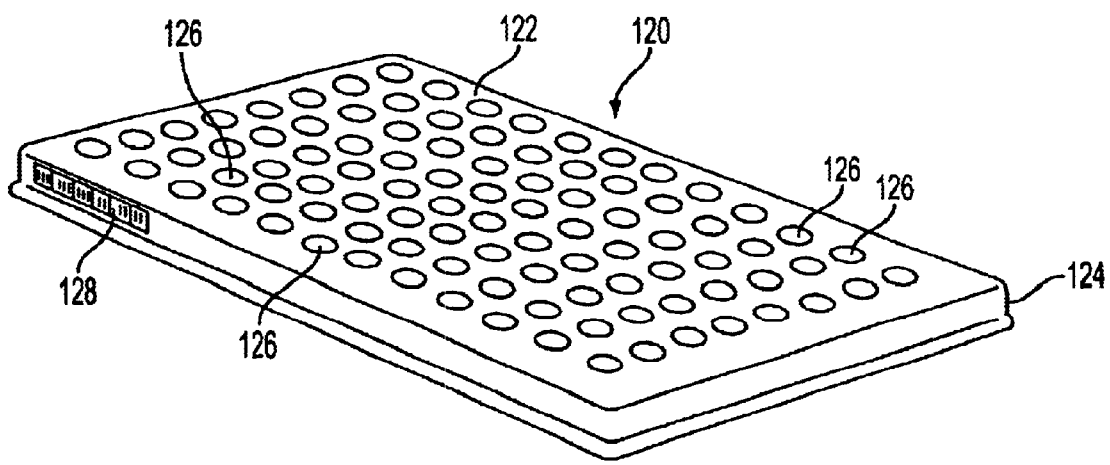
FIG. 8 is a perspective view of a multiwell plate in one embodiment of the invention.
Figure 9:
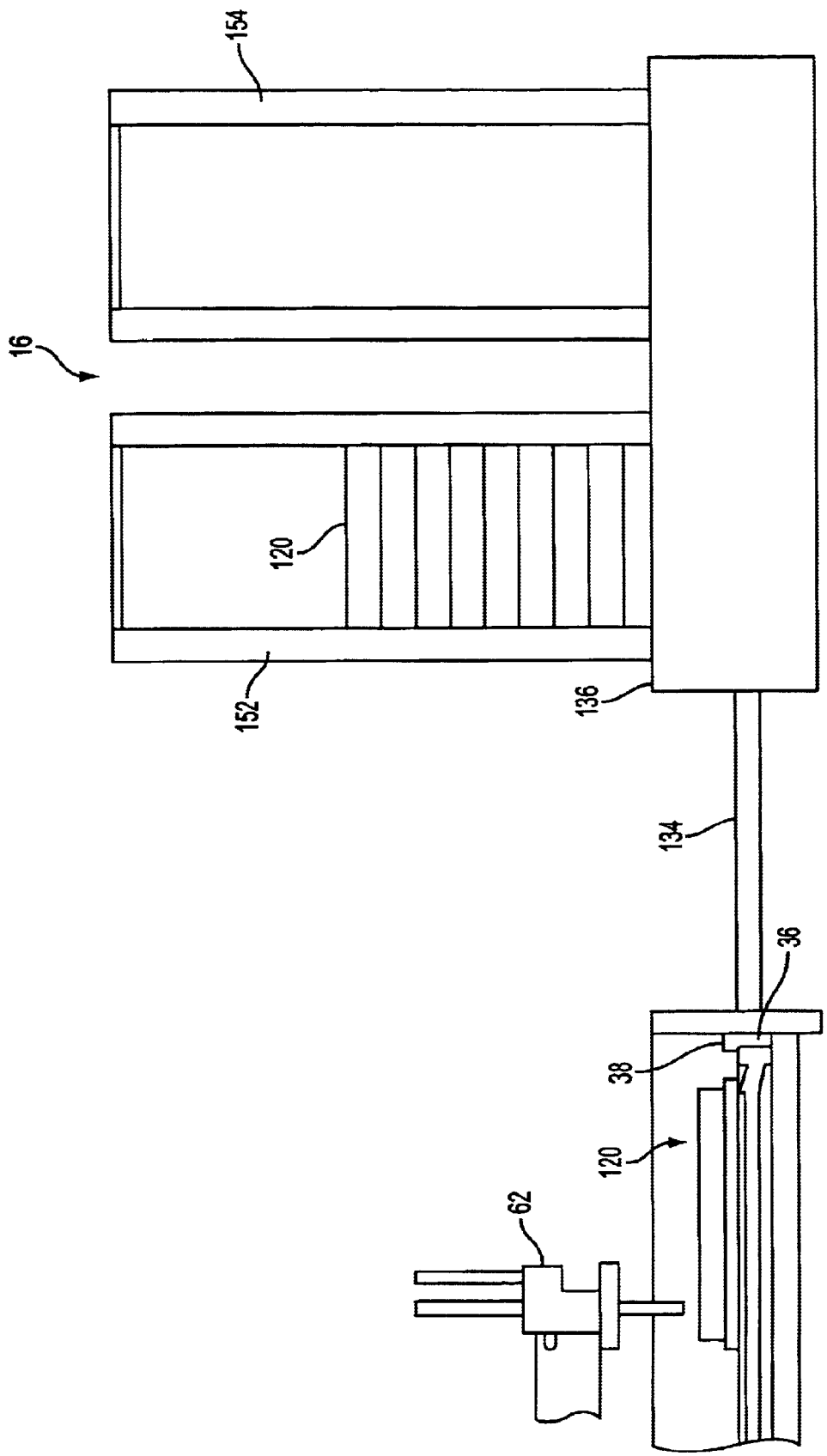
FIG. 9 is a front view of the cutting assembly and plate stacking assembly in a preferred embodiment of the invention.

Apparatus 10 is primarily programmed by computer 20 to excise selected portions or samples from gel 98 and automatically transfer the excised portion to a sample receiving tray 120. As shown in FIG. 8, tray 120 is a standard multiwell sample plate as known in the art. Tray 120 typically has a substantially rectangular shape with a top face 122 and side walls 124. A plurality of spaced-apart wells 126 are formed in top face 122 and are dimensioned to contain a sufficient volume of a sample, typically about 10 to about 50 microliters. In one embodiment of the invention, sample tray 120 contains an array 96 of wells 126 arranged in rows and columns. The number of wells 126 in tray 120 can vary depending on the manufacturer of the tray, the nature of the samples being analyzed and the process for carrying out the analysis of the sample. Preferably, a bar code 128 is provided on a side wall 124 to identify the respective tray 120 and the samples contains in wells 126. Bar code 128 can be used to track the location of the tray within the apparatus and for cataloging the samples cut from the gel slab.

Imaging device 14 can be a commercially available device capable of scanning a two dimensional electrophoresis gel and generating an image signal that is transmitted to computer 20. Imaging device 14 as shown in FIGS. 1 and 3, includes a front opening 130 for receiving tray 34. In this manner, an electrophoresis gel 98 is supported on plate 92 of tray 34 and is inserted through opening 130 of imaging device 14. Imaging device 14 then scans an image to obtain an image signal and processes the image signal to identify the location of the macromolecule samples that have been separated by the electrophoresis separation process. Prior to scanning gel 98, the separated macromolecules in the gel are stained with a visual stain or a fluorescent stain as known in the art for electrophoresis separation and analysis processes.

Referring to FIGS. 4 and 9–15, storage assembly 16 is coupled to cutting assembly 12 for sequentially supplying a sample tray 120 for receiving gel samples excised from gel slab 98. Storage assembly 16 includes a support surface 134 extending from a housing 136. Support 134 extends through an opening 138 in side wall 28 of housing 22 of cutting assembly 12. Support 134 has a top surface preferably lying in the same plane as base 26 and is positioned adjacent recessed area 42. Base 26 of cutting assembly 12 has a recess 143 to accommodate support surface 142. In one embodiment, a recess 145 is provided adjacent support surface 142. Recess 145 includes an inclined bottom wall 147 that slopes toward an opening 149 to drain any spilled liquids from the base 26. A suitable collection vessel can be placed below opening 149 to collect the liquids.

Figure 10:
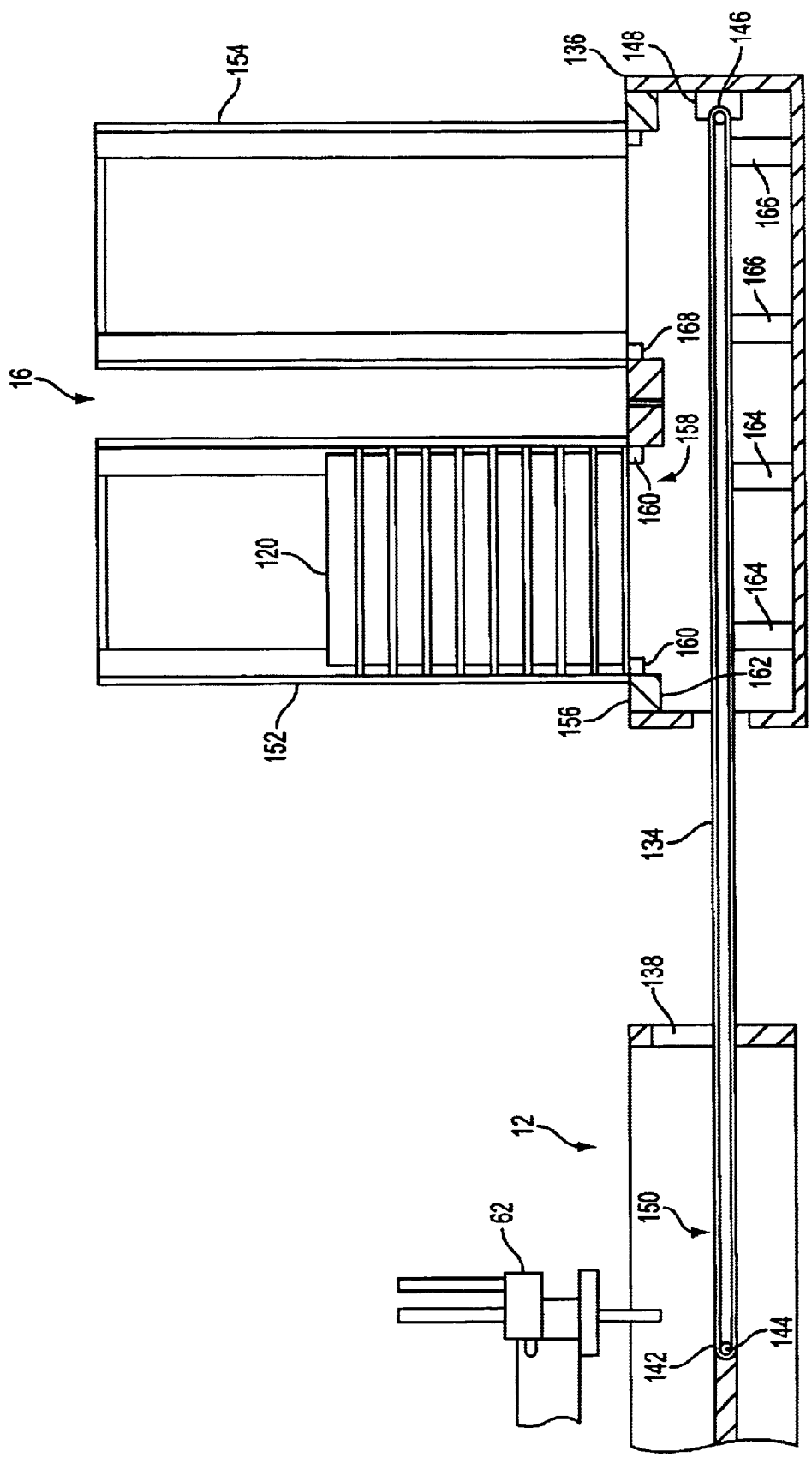
FIG. 10 is a partial cross-sectional side view of the cutting assembly and plate stacking assembly of FIG. 9.

Support 134 includes a conveyor 140 extending between housing 136 and an outer end 142 of support 134. In the embodiment illustrated, conveyor 140 is a continuous belt extending from outer end 142 of support 134 and housing 136 as shown in FIG. 10. Conveyor 140 is typically a belt having a width that is less than a width of support 134. An idle pulley 144 as shown in FIG. 10 is mounted at outer end 142 to support and to guide conveyor 140. A drive pulley 146 coupled to a motor 148 is mounted in housing 136 to drive conveyor 140. Preferably, motor 148 is a dual directional motor capable of moving conveyor 140 in two directions at controlled increments.

Outer end 142 of support 134 defines a work station 150 for receiving a sample tray 120 during the cutting and loading operation of cutting assembly 12. Storage assembly 16 includes a supply magazine 152 and a receiving magazine 154 coupled to housing 136. As shown in FIG. 10, housing 136 includes a top wall 156 having an opening 158 dimensioned to enable a sample tray 120 to pass through. Supply magazine 152 contains a plurality of stacked sample trays 120 which can be dispensed sequentially through opening 158. Detents 160 extend into opening 158 to support the stack of sample trays 120. Detents 160 are coupled to a respective actuator 162 and are retracted to allow a sample tray 120 to pass through opening 158. Actuators 162 are operatively connected to computer 20 to coordinate the dispensing of a sample tray 120 with the cutting operation.

Figure 11:
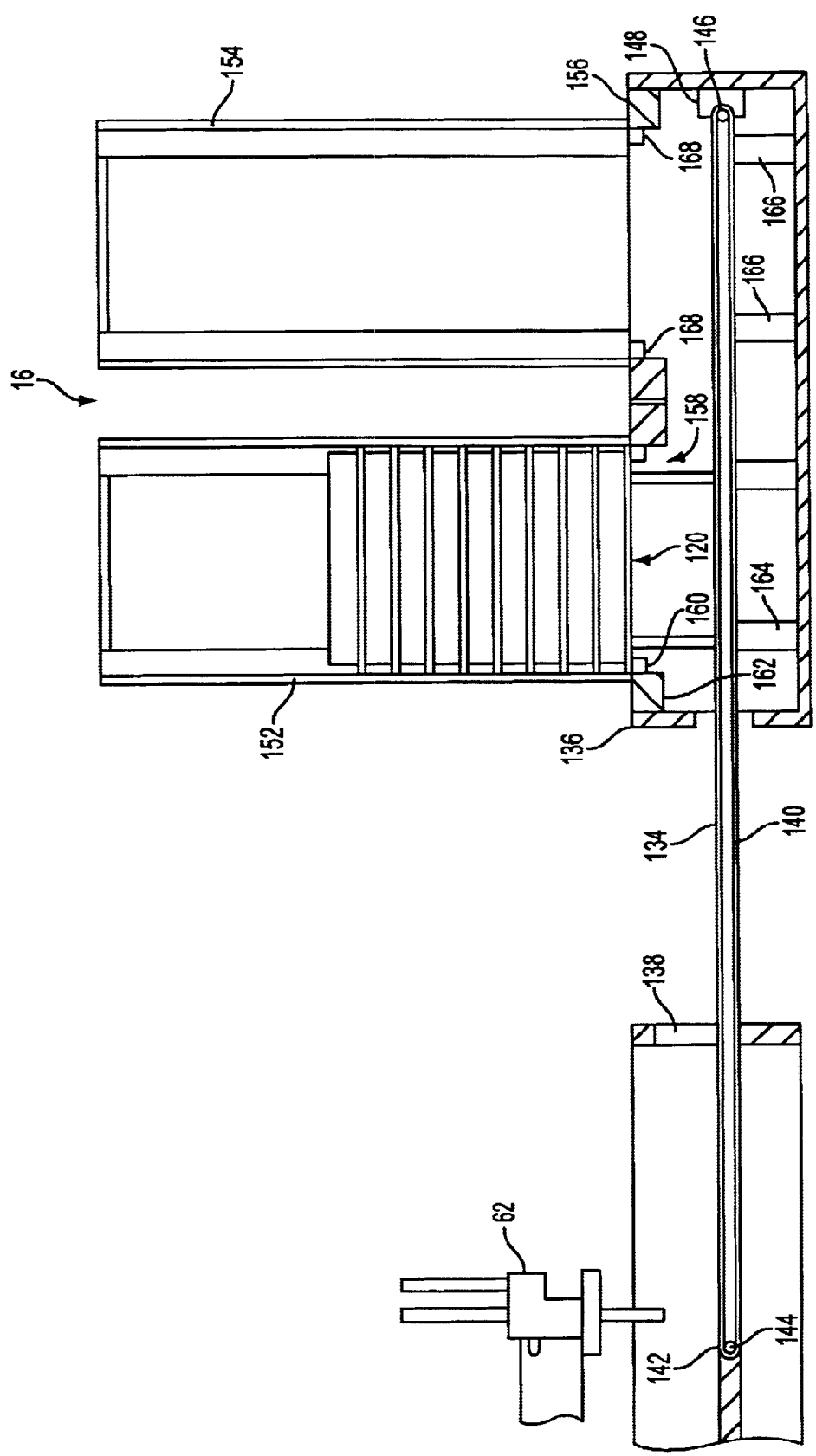
FIG. 11 is a partial cross-sectional side view of the cutting assembly and stacking assembly showing the actuating pistons in the extended position.
Figure 12:
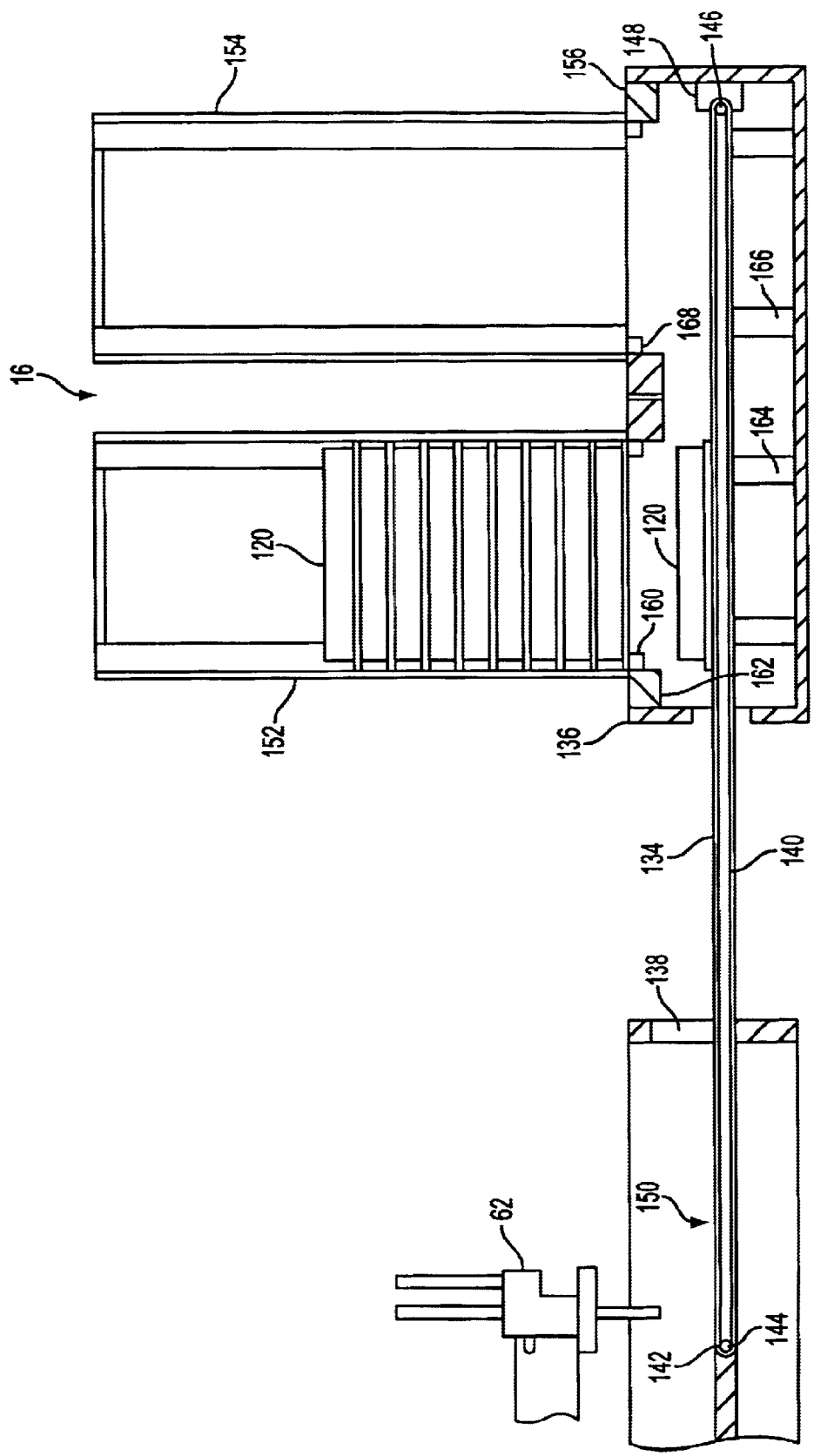
FIG. 12 is a partial cross-sectional side view of the cutting assembly and stacking assembly showing a multiwell plate lowered from a supply magazine onto the conveyor.
Figure 13:
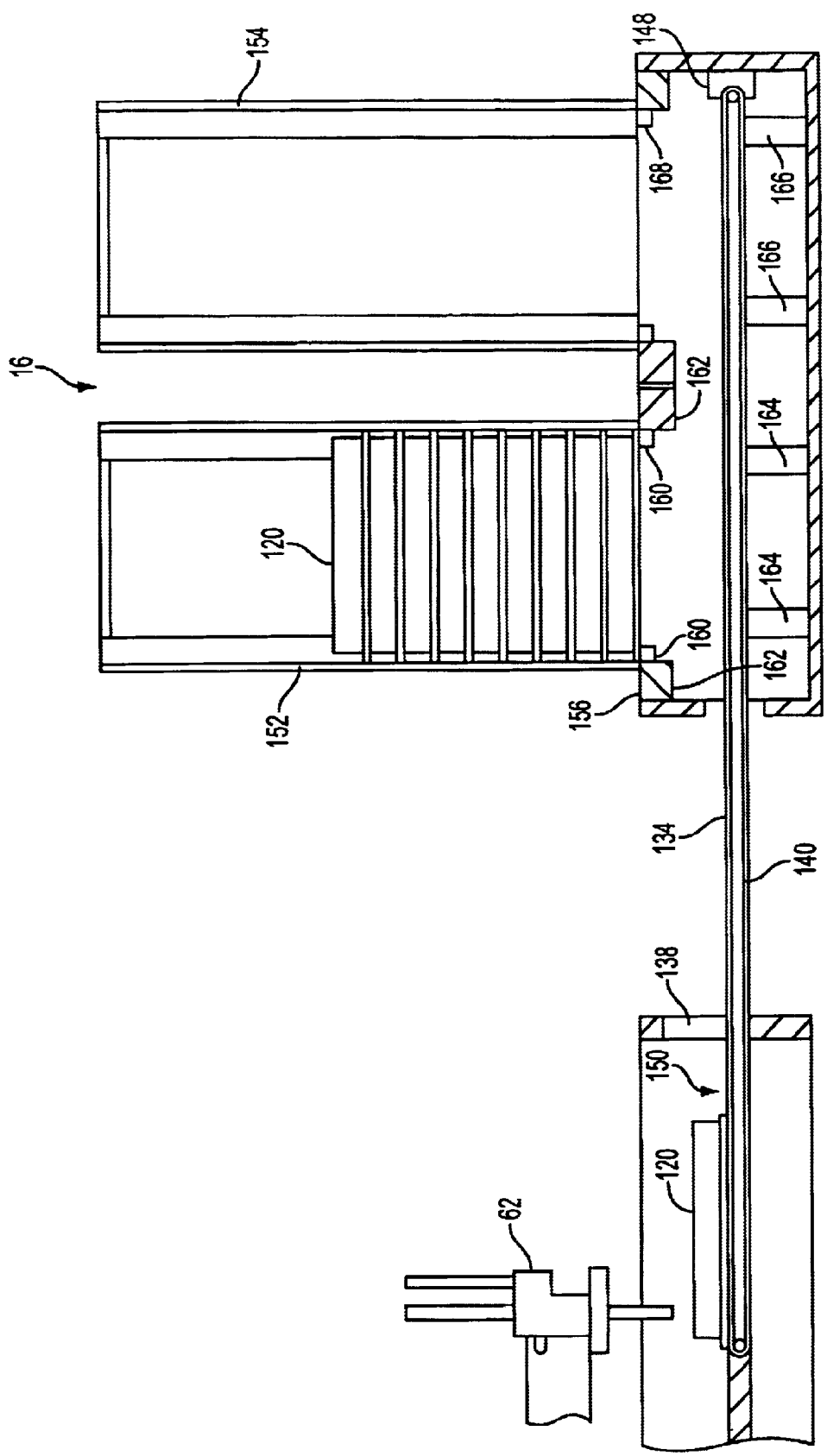
FIG. 13 is a partial cross-sectional side view of the cutting assembly and stacking assembly showing the multiwell plate positioned in the cutting assembly.

Storage assembly 16 includes four pneumatic plungers 164 positioned below supply magazine 152. Plungers 164 can be extended upwardly to engage the stack of sample trays 120 in supply magazine 152 as shown in FIG. 11. In operation, plungers 164 are extended to the position shown in FIG. 11 and detents 160 are retracted to release a single sample tray 120. Plungers 164 are then retracted to lower a sample tray 120 onto conveyor 140. Conveyor motor 148 is actuated to convey sample tray 120 to work station 150 as shown in FIG. 13. Motor 148, detents 160 and plungers 164 are controlled by a suitable microprocessor which is ultimately controlled by computer 20 to coordinate the delivery of a sample tray 120 to work station 150 with the cutting of the gel. Robotic arm assembly 24 is then actuated by computer 20 to excise predetermined samples from gel 98 and sequentially transfer the excised portion to a respective well 126 of sample tray 120.

Figure 14:
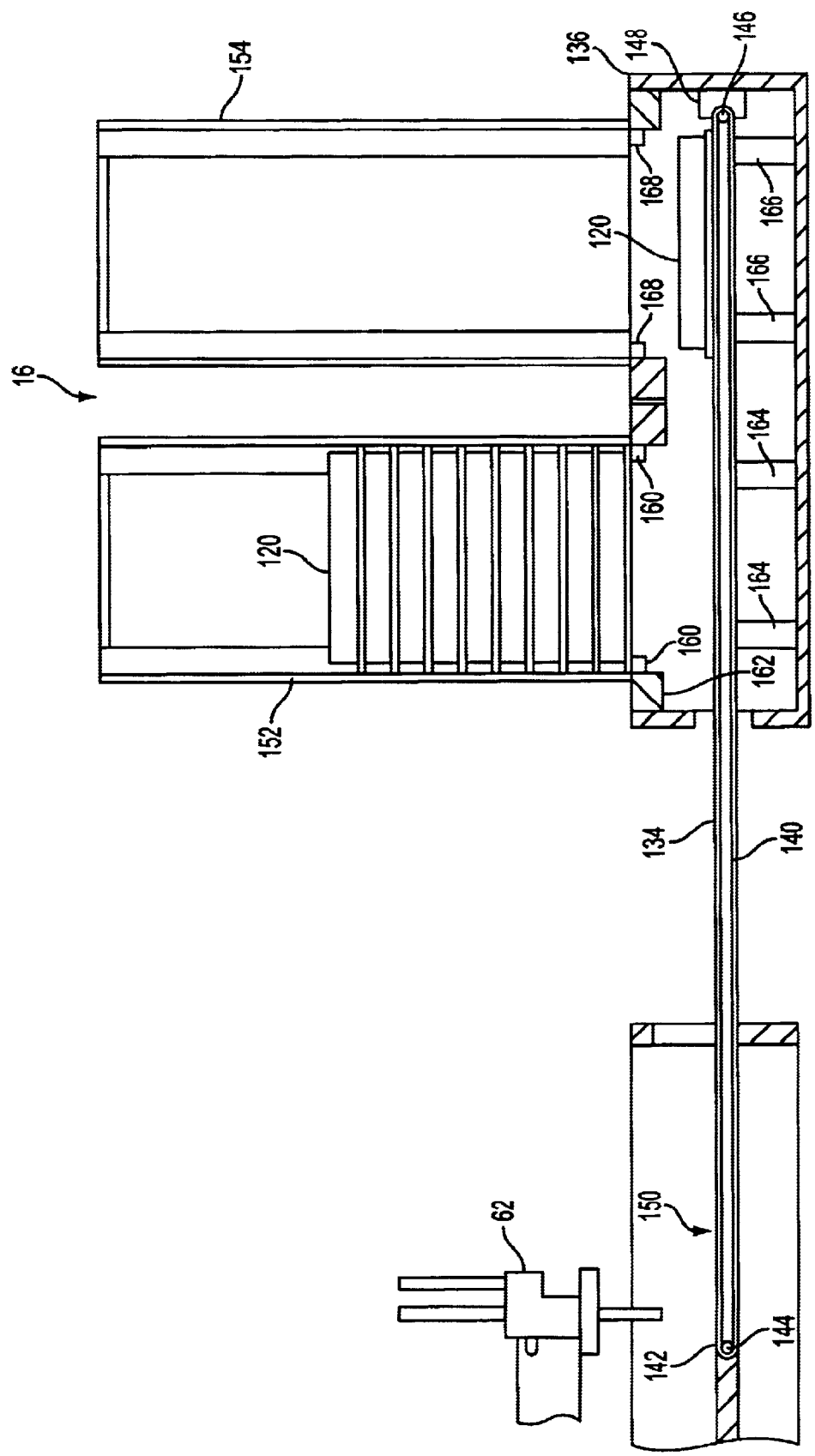
FIG. 14 is a partial cross-sectional side view of the cutting assembly and stacking assembly showing the multiwell plate in position for feeding to a storage magazine.
Figure 15:
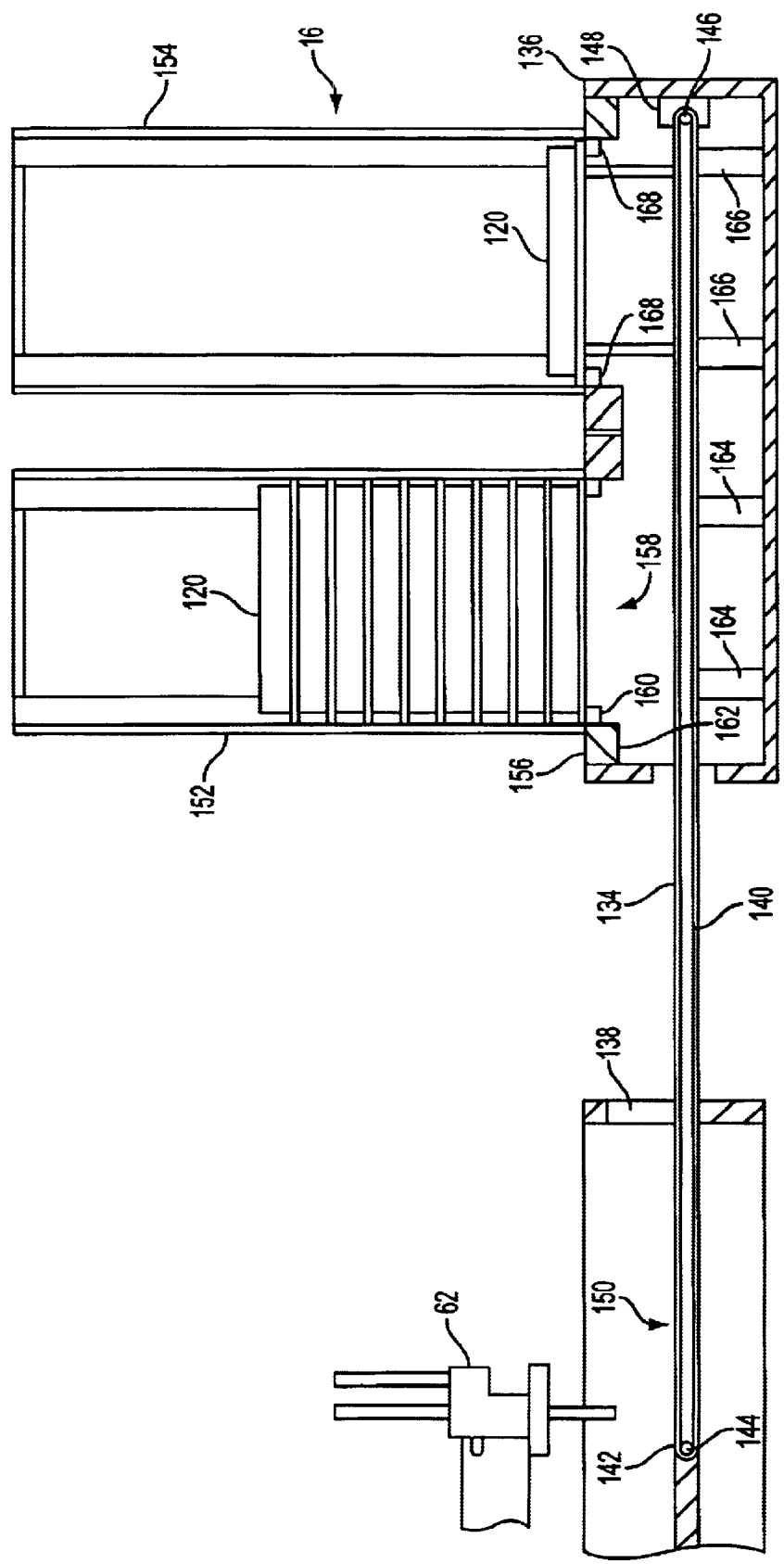
FIG. 15 is a partial cross-sectional side view of the cutting assembly and stacking assembly showing the multiwell plate raised to the storage position in a storage magazine.

After the excised samples from gel 98 are transferred to sample tray 120, conveyor motor 148 is actuated to convey sample tray 120 to a position below receiving magazine 154 as shown in FIG. 14. Plungers 166 positioned below receiving magazine 154 are actuated to push sample tray 120 upwardly into receiving magazine 154. Detents 168 retain sample tray 120 in receiving magazine 154. One example of a suitable storage assembly that can be used in combination with cutting assembly 12 is available from Packard Biosciences Corporation and is sold under the tradename Platestack.

The method of the invention is carried out using apparatus 10 to identify selected samples in a second dimension electrophoresis gel, automatically excise the sample from the gel and transfer the excised portion to a sample tray. In the embodiment illustrated, electrophoresis gel 98 is positioned on plate 92 of tray 34 either manually or by use of a suitable robotic assembly (not shown). Typically, electrophoresis gel 98 is an acrylamide gel as known in the art. Electrophoresis gel 98 is positioned on plate 92 and sticks to the surface of place 92 by the tackiness of the gel. Preferably, gel 98 is coupled to a gel clamp 100 which fits in recessed area 84 to prevent movement of gel 98 on plate 92.

In one embodiment of the invention, tray 34 is manually placed in imaging device 14 by sliding tray through opening 130. As shown in FIG. 6, side edges 68 of tray 34 include a substantially V-shaped recess 170. Imaging device 14 preferably includes a suitable detent to engage recess 170 to position tray 34 and gel 98 in a predetermined location within imaging device 14. Imaging device 14 then scans gel 98, records an image and produces an image signal of gel 98. The image signal identifies the location of predetermined samples and is processed to determine position coordinates identifying the position of the samples on the gel. The image signal is transmitted to computer 20 which processes the image signal to calculate the coordinates for directing the cutting arm for excising the selected samples.

Figure 5A:
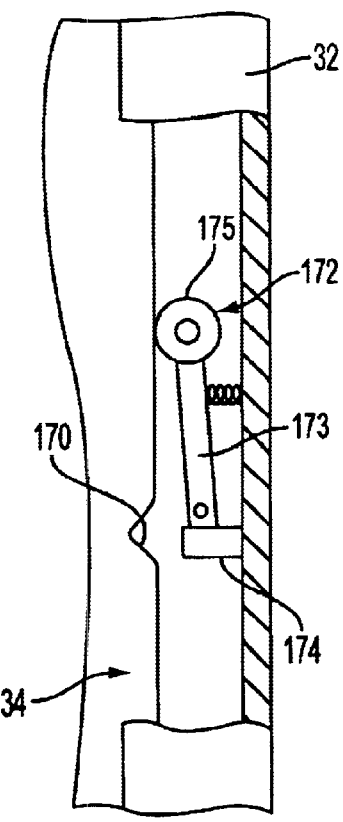
FIGS. 5A and 5B are partial top views of coupling and indicator members for indicating proper position of the tray in the cutting assembly.
Figure 5B:
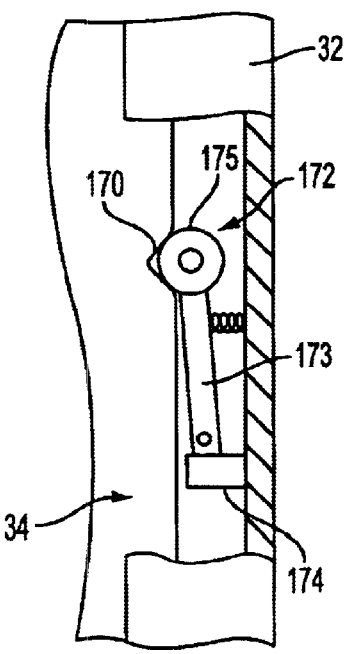

Tray 34 is then removed from imaging device 14 and transferred to cutting assembly 12. Tray 34 slides between guide rails 32 of cutting assembly into a position for excising samples from gel 98. As shown in FIGS. 5A and 5B, guide rail 32 includes a spring biased detent 172 to engage recess 170 of tray 34 to position tray 34 in a specific location in cutting assembly 12. In one embodiment of the invention, detent 172 is a spring biased, pivotally mounted arm 173 having a roller 175 that allows tray 34 to be inserted and removed from guide rails 32. Preferably, detent 172 includes a microswitch 174 which is operatively connected to computer 20 and produces a positioning signal to indicate that tray 34 is properly positioned in cutting assembly 12.

Once tray 34 is properly positioned in cutting assembly 12 as indicated by microswitch 174, computer 20 actuates robotic arm assembly 24 to move first arm 48 and second arm 56 simultaneously to position cutting head 62 in a selected location above gel 98 corresponding to the location of a selected sample to be excised. Computer 20 then actuates cutting head 62 to excise a portion of gel 98 containing the selected macromolecule sample to be excised. Robotic arm assembly 24 is then actuated to move cutting head 62 to a position above a selected well 126 of sample tray 120 to dispense the excised sample into well 126. The operation is repeated until each well 126 of sample tray 120 receives a selected sample excised from gel 98. A signal can be generated by cutting assembly 12 and processed by computer 20 indicating sample tray 120 being filled.

Computer 20 actuates conveyor motor 148 to convey the filled sample tray to the position shown in FIG. 14 where plungers 166 lift sample tray 120 into receiving magazine 154. An empty sample tray 120 is then dispensed from supply magazine 152 and conveyed to work station 150 so that the sample tray can be filled with the selected excised samples from gel 98. Preferably, computer 20 receives a positioning signal from cutting assembly 12 or storage assembly 16 to indicate a sample tray 120 being present in work station 150.

Figure 16:
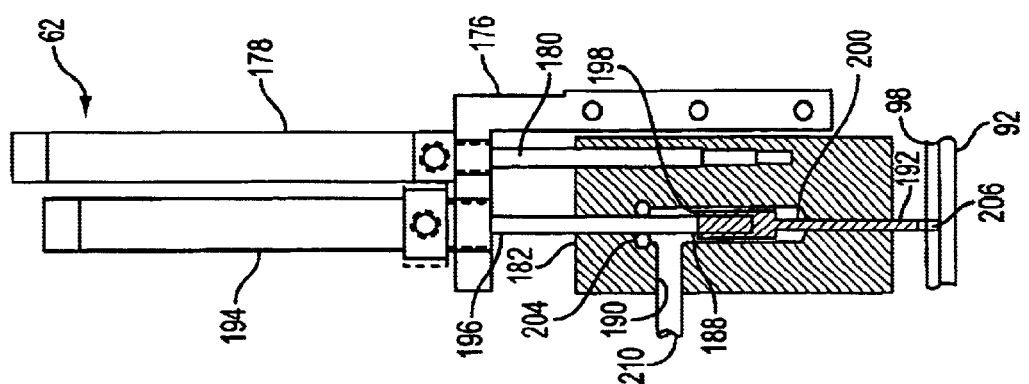
FIG. 16 is a partial cross-sectional side view of the cutting head of the cutting assembly showing the cutting head in a retracted position.
Figure 17:
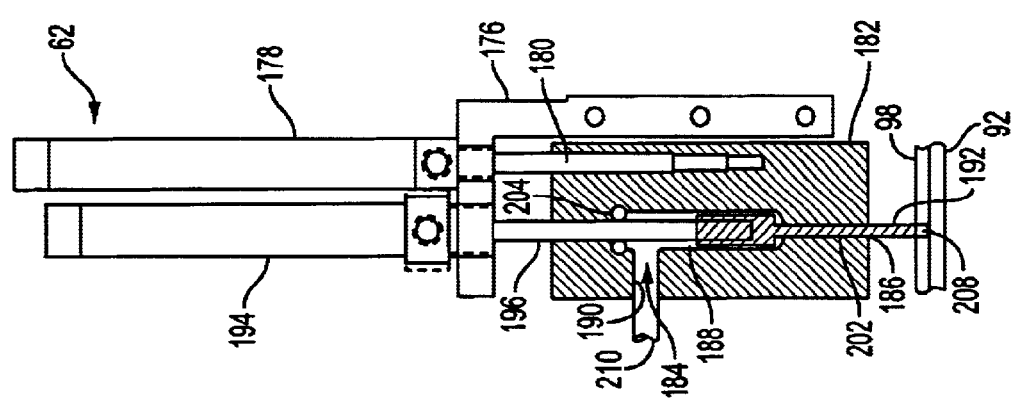
FIG. 17 is a cross-sectional side view of the cutting head of FIG. 16 showing the plunger in contact with the electrophoresis gel.

Cutting head 62 can be any suitable device capable of excising a selected portion of gel 98 and transferring the excised portion to a sample tray 120. In a preferred embodiment of the invention, cutting head 62 includes a support arm 176 coupled to second arm 56 of robotic arm assembly 24. An actuator in the form of a pneumatic cylinder 178 having a retractable piston rod 180 is coupled to support 176 as shown in FIGS. 16 and 17. Rod 180 is coupled to a supporting block 182 for reciprocating supporting block 182 with respect to support 176. Block 182 includes an internal passage 184 having a bottom end 186, a cylindrical internal cavity 188 and a supply passage 190. A hollow tubular cutting punch 192 extends downwardly from bottom end 186 and is in communication with cavity 188 and internal passage 184.

A pneumatic cylinder 194 having a reciprocating rod 196 is coupled to support 176 as shown in FIG. 16. A piston 198 having a plunger rod 200 is coupled to rod 196 for reciprocal movement in cavity 188. Plunger rod 200 is mounted for reciprocal movement through axial passage 202 of punch 192. In the embodiment illustrated, a seal 204, such as an O-ring, surrounds rod 196 to prevent the flow of fluid from cavity 188 along the axial passage which receives rod 196.

Figure 18:
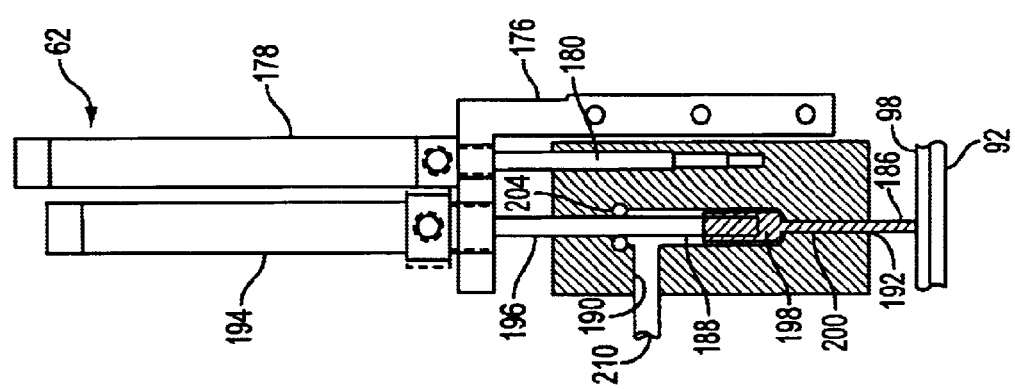
FIG. 18 is a cross-sectional side view of the cutting head showing the cutting sleeve penetrating the electrophoresis gel.
Figure 19:
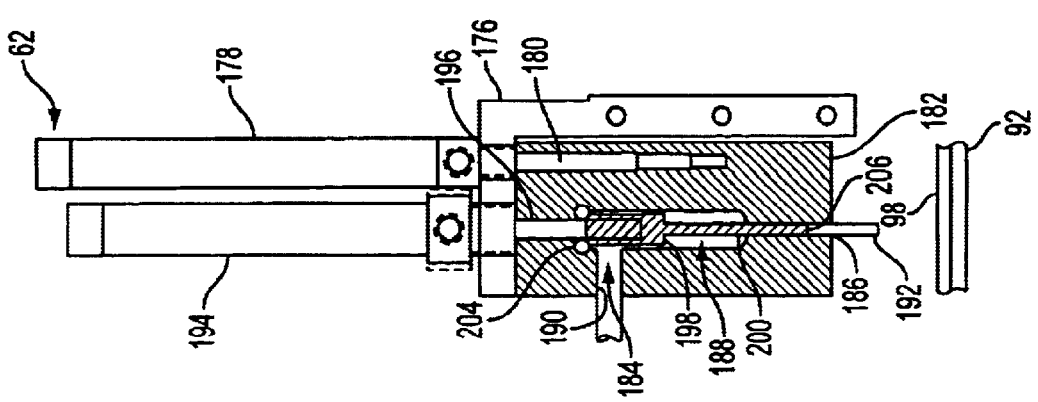
FIG. 19 is a cross-sectional side view of the cutting head showing the plunger retracting the cut gel sample from the electrophoresis gel.
Figure 21:
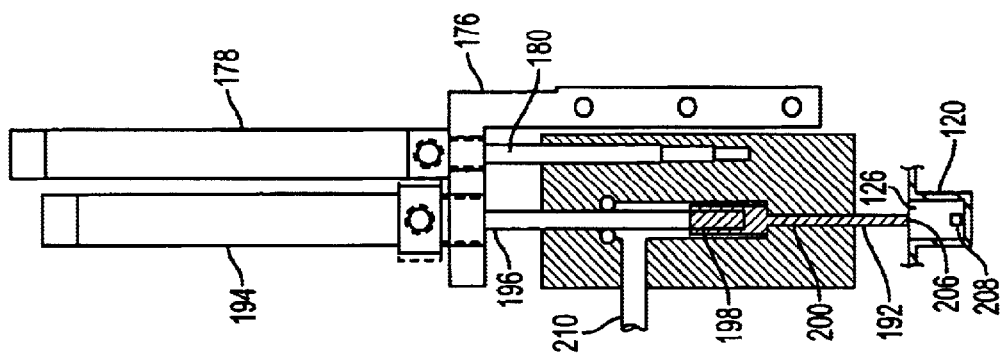
FIG. 21 is a cross-sectional side view of the cutting head showing the gel sample dispensed from the cutting head into the storage container.

In operation, cutting assembly 62 is positioned above gel 98 to excise the sample identified by imaging device 14. Pneumatic cylinder 194 is actuated to extend plunger rod 200 so that the axial tip 206 of plunger rod 200 extends from the axial end of punch 192. Pneumatic cylinder 198 is actuated to lower block 182 until the axial tip 206 of plunger rod 200 contacts the top surface of gel 98 as shown in FIG. 17. Preferably, axial tip 206 contacts gel 98 substantially without deforming gel 98. Pneumatic cylinder 178 then lowers block 182 so that punch 192 penetrates gel 98 and contacts support plate 92 to cut gel 98 as shown in FIG. 18. Pneumatic cylinder 194 is then actuated to raise plunger rod 200 and retract plunger rod 200 with respect to punch 192 to create a suction within punch 192 and pull the excised gel piece 208 into punch 192 as shown in FIG. 19.

Figure 20:
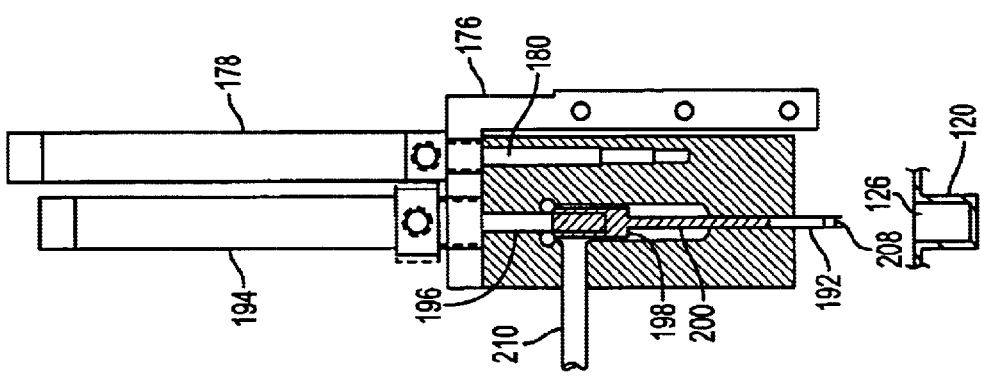
FIG. 20 is a cross-sectional side view of the cutting head showing the captured gel sample and where the cutting head is positioned above a sample container.

Robotic arm assembly 24 then moves cutting head 62 to a position shown in FIG. 20 directly above a selected well of a sample tray 120. Pneumatic cylinder 194 is actuated to extend plunger rod 200 to eject gel piece 208 from punch 192 into well 126. In a preferred embodiment, a wash liquid such as deionized water is introduced through a supply conduit 210 which flows through cavity 188 and through a small gap between plunger rod 200 and punch 192 to assist in ejecting gel piece 208 from punch 192 and to wash any residue from plunger rod 200 and punch 192. The sequence is repeated until each identified sample is cut from gel 98 and transferred to a respective well in a sample tray.

After the selected samples are cut from the gel, tray 36 is removed from cutter 12 and the spent gel is discarded. Tray 36 is rinsed with a suitable wash liquid to remove traces of the gel and other materials that interfere with the subsequent protein analysis. Tray 36 receives a fresh gel and the process steps are repeated.

While several embodiments of the invention have been described herein, it will be appreciated that various changes and modifications can be made without departing from the scope of the invention as defined in the appended claims.

What is claimed is:

1. An apparatus for excising a plurality of samples from an electrophoresis gel, said apparatus comprising:

a base having a work surface with a loading station dimensioned to support a sample plate having a plurality of sample-receiving wells;

a gel support member removably coupled to said base, said support member comprising a removable tray having a substantially planar surface for supporting said gel in a substantially flat condition and having a coupling member capable of coupling said tray to a robotic tray-manipulating member;

a computer controlled robotic arm assembly having an operating head for excising a plurality of predetermined samples from said gel while said gel is supported on said gel support member and transferring said predetermined samples to a respective well of said sample plate, said robotic arm assembly having a first arm with a first end and a second end, a first motor coupled to said first end of said first arm and oriented to pivot said first arm about an axis perpendicular to a plane of said base, a second motor coupled to said second end of said first arm, a second arm having a first end and second end, said first end of said second arm being coupled to said second motor and being pivotable about an axis perpendicular to said base, and wherein said operating head is coupled to said second end of said second arm;

a microprocessor operatively coupled to said robotic arm for controlling movement of said robotic arm, said microprocessor being programmed to receive a signal for identifying said predetermined samples on said gel, actuating said robotic arm to excise said predetermined samples, and transferring said samples to said respective well of said sample plate; and an imaging device for obtaining an image of said gel, identifying a plurality of sample locations on said gel, and producing an image signal corresponding to said sample locations, said imaging device being separate from said base and robotic arm of said apparatus and being operatively coupled to said microprocessor whereby said microprocessor receives said image signal and actuates said robotic arm to excise said sample locations.

2. The apparatus of claim 1, wherein said coupling member of said tray has an aperture for coupling with said tray-manipulating assembly.

3. The apparatus of claim 1, wherein said tray has a top surface, and wherein said substantially planar surface is defined by a flat plate coupled to said top surface.

4. The apparatus of claim 3, wherein said plate is a glass plate.

5. The apparatus of claim 4, wherein said glass plate defines a support surface for supporting said gel while excising said samples.

6. The apparatus of claim 1, wherein said tray has a first end for receiving and supporting said gel, a second end opposite said first end, a first side edge and a second side edge, said tray further having a first area spaced between said first end and said second end, said first area being dimensioned to receive a gel handling device.

7. The apparatus of claim 6, wherein said gel is coupled to said gel handling device, said gel handling device being dimensioned to fit in said first area to enable said gel to lay directly on said planar surface of said tray.

8. The apparatus of claim 6, wherein said first area includes at least one aperture.

9. The apparatus of claim 8, wherein said first area of said tray has two spaced apart apertures dimensioned to receive a coupling assembly of a robotic arm.

10. The apparatus of claim 6, wherein said first and second sides of said tray include an inwardly facing notch dimensioned to support said gel handling device.

11. The apparatus of claim 6, wherein said first area is recessed with respect to said planar surface.

12. The apparatus of claim 6, wherein said first side edge of said tray includes an outwardly facing first recess, and wherein said housing includes a first moveable coupling member for engaging said recess to locate said tray in said base in a selected location.

13. The apparatus of claim 12, wherein said first coupling member is a spring biased detent.

14. The apparatus of claim 6, wherein said planar surface is spaced from said first side edge and said second side edge, said tray further comprising a plurality of liquid channels extending between said first side edge and said planar area and between said second side edge and said planar surface.

15. The apparatus of claim 1, wherein said imaging device is an imaging scanner having an imaging area dimensioned to receive said removable gel support member.

16. The apparatus of claim 1, further comprising a storage assembly for storing a plurality of said sample plates, said storage assembly having a conveyor extending between said storage assembly and said top surface of said base.

17. The apparatus of claim 16, wherein said storage assembly includes a supply magazine for storing said sample plates and a receiving magazine for receiving sample plates from said base.

18. The apparatus of claim 17, wherein said storage assembly is operatively coupled to said microprocessor, and wherein said microprocessor is programmed to dispense a sample plate from said supply magazine to said loading station, actuate said robotic arm to transfer said samples into a respective well of said sample plate and to transfer said sample plate from said loading station to said receiving magazine.

19. The apparatus of claim 1, wherein said microprocessor identifies a location of said predetermined samples in said gel based on polar coordinates.

20. The apparatus of claim 19 wherein said recessed area of said tray has a depth substantially equal to a thickness of said first clamping jaw.

21. The apparatus of claim 1, further comprising a gel clamp having first and second pivotally connected clamping jaws each having a gripping end, an electrophoresis gel having one end gripped between said first and second gripping ends, and wherein said tray has a planar area supporting said gel in a flat condition and having a recessed area having a dimension to receive said first clamping jaw whereby said gel lays flat on said planar area.

22. The apparatus of claim 1, wherein said base included two parallel guide rails spaced apart a distance to receive and position said removable try in an operating position and where said base includes a microswitch operatively connected said microprocessor and produces a positioning signal indicating said tray is in said operating condition.

23. An apparatus for excising a plurality of biological samples from an electrophoresis gel, said apparatus comprising:
   a gel support member having a planar surface with a dimension for supporting an electrophoresis gel in a substantially flat condition;
   a base having a work surface with a loading station dimensioned to removably receive and support said gel support member for said electrophoresis gel and a sample plate having a plurality of sample-receiving wells;
   a scanning device separate from said base, said scanning device having a dimension to receive said gel support member and said electrophoresis gel for capturing an image of said gel and producing an image signal corresponding to said image, said gel support member being movable between said scanning device and said base;
   an automated sample plate handling assembly coupled to said base, said plate handling assembly including a supply magazine for containing a plurality of empty sample plates, a receiving magazine for receiving filled sample plates, and a conveyor for sequentially conveying a sample plate from said supply magazine to said loading station and for conveying said sample plate from said loading station to said receiving magazine;
   a robotic arm having an operating head for excising a plurality of predetermined samples from said gel and for transferring said excised samples to a respective well of a sample plate positioned in said loading station; and
   a microprocessor operatively connected to said robotic arm for controlling movement of said robotic arm and being operatively connected to said scanning device, said microprocessor being programmed to receive said image signal from said scanning device and identifying said predetermined samples on said gel and actuating said robotic arm to excise said respective predetermined samples and transferring said predetermined samples to said respective well of said sample plate, said microprocessor further being operatively connected to said sample plate handling assembly for actuating said handling assembly to deliver said empty sample plates sequentially from said supply magazine to said loading station and for conveying said sample plate from said loading station to said receiving magazine after receiving said predetermined samples.

24. The apparatus of claim 23, further comprising an electrophoresis gel, wherein said gel support member is a tray having a first end receiving and supporting said gel, a second end opposite said first end, a first side edge and a second side edge, said tray further having a first recessed area spaced from said first end and dimensioned to receive a gel handling device.

25. The apparatus of claim 24, wherein said gel handling device is a clamp having a first and a second clamping jaw pivotally connected together and where said gel is clamped between said jaws, and wherein said first jaw of said clamp is dimensioned to fit in said first area to enable said gel to lay directly on said tray.

26. The apparatus of claim 25, wherein said first and second sides of said tray include an inwardly facing notch dimensioned to support said gel clamp.

27. The apparatus of claim 24, wherein said first area includes at least one aperture.

28. The apparatus of claim 27, wherein said first area of said tray has two spaced apart apertures dimensioned to receive a coupling assembly of a robotic arm.

29. The apparatus of claim 24, wherein said first side edge of said tray includes an outwardly facing first recess, and wherein said base includes a first moveable coupling member for engaging said recess to locate said tray on said housing in a selected location.

30. The apparatus of claim 29, wherein said coupling member is a spring biased detent.

31. The apparatus of claim 24, wherein said planar area is spaced from said first side edge and said second side edge, said tray further comprising at least one liquid channel extending between said first side edge and said planar area and between said second side edge and said planar area.

32. The apparatus of claim 23, wherein said base includes two parallel guide rails spaced apart a distance to removably receive said gel support member and position said gel support member is an operating position in said base, and where said base includes a microswitch operatively connected to said microprocessor and produces a positioning signal indicating said tray is in said operating condition.

33. The apparatus of claim 23, wherein said microprocessor identifies a location of said predetermined samples in said gel based on polar coordinates.

34. An apparatus for excising a plurality of samples from an electrophoresis gel, said apparatus comprising:
- a base having a work surface with a loading station dimensioned to support a sample plate having a plurality of sample-receiving wells;
- a gel support tray removably coupled to said base, said tray having a top surface, with a first end and a second end and a support plate coupled to said first end of said top surface for supporting said gel in a substantially flat condition, and a recessed area at said second end and having a dimension for receiving a gel handling device that is removably coupled to said gel, whereby said gel handling device fits in said recessed area to enable said gel to lay flat directly on said support plate, said base having first and second parallel guide rails for guiding said gel support tray to an operating position for excising said samples from said gel,
- a computer controlled robotic arm assembly having an operating head for excising a plurality of predetermined samples from said gel while said gel is supported on said gel support member and said tray is in said operating position, and for transferring said predetermined samples to a respective well of said sample plate; and
- a microprocessor operatively coupled to said robotic arm for controlling movement of said robotic arm, said microprocessor being programmed to receive a signal for identifying said predetermined samples on said gel, actuating said robotic arm to excise said predetermined samples, and transferring said samples to said respective well of said sample plate.

35. The apparatus of claim 34, wherein said second end of said tray includes at least one aperture for coupling said tray to a robotic tray-manipulating assembly.

36. The apparatus of claim 34, wherein said support plate is a glass plate.

37. The apparatus of claim 34, wherein said recessed area includes at least one aperture.

38. The apparatus of claim 34, wherein said recessed area of said tray has two spaced apart apertures dimensioned to receive a coupling assembly of a robotic arm.

39. The apparatus of claim 34, wherein said first and second sides of said tray include an inwardly facing notch in said recessed area dimensioned to support said gel handling device.

40. The apparatus of claim 34, wherein said tray has a first side edge and a second side edge cooperating with said guide rails, said first side edge having a first recess, and wherein said base includes a first movable coupling member for engaging said recess to locate said tray on said base in said operating position, and where said coupling member is operatively connected to said microprocessor whereby said microprocessor operates said robotic arm only when said tray is in said operating position.

41. The apparatus of claim 40, wherein said first coupling member is a spring biased detent and is movable from a first position to a second position received in said first recess.

42. The apparatus of claim 40, wherein said support plate is spaced from said first side edge and said second side edge, said tray further comprising a plurality of liquid channels extending between said first side edge and said planar area and between said second side edge and said support plate.

43. The apparatus of claim 40, wherein said first movable coupling member includes a microswitch operatively connected to said microprocessor, said microswitch position signal indicating said tray is in said operating position.

44. The apparatus of claim 34, wherein said microprocessor identifies a location of said predetermined samples based on polar coordinates.

* * * * *

UNITED STATES PATENT AND TRADEMARK OFFICE
CERTIFICATE OF CORRECTION

PATENT NO. : 6,652,724 B2
DATED : November 25, 2003
INVENTOR(S) : Michael et al.

It is certified that error appears in the above-identified patent and that said Letters Patent is hereby corrected as shown below:

Column 1,
Line 9, insert -- This invention was made with United States Government support under cooperative agreement number 70NANB5H1075 awarded by the National Institute of Standards and Technology. The government has certain rights in the invention. --.
Line 24, delete "condons" and insert -- codons --.

Signed and Sealed this

Twenty-second Day of November, 2005

JON W. DUDAS
*Director of the United States Patent and Trademark Office*